United States Patent
Witt et al.

(10) Patent No.: US 9,642,941 B2
(45) Date of Patent: May 9, 2017

(54) IMPLANTABLE MODULAR HYDROGEL FOR SALIVARY GLAND RESTORATION

(71) Applicants: WILLIAM MARSH RICE UNIVERSITY, Houston, TX (US); UNIVERSITY OF DELAWARE, Newark, DE (US)

(72) Inventors: Robert L. Witt, Kennett Square, PA (US); Xinqiao Jia, Newark, DE (US); Swati Pradham Bhatt, Newark, DE (US); Mary C. Farach-Carson, Houston, TX (US); Daniel A. Harrington, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 24 days.

(21) Appl. No.: 14/305,424

(22) Filed: Jun. 16, 2014

(65) Prior Publication Data
US 2014/0294960 A1  Oct. 2, 2014

Related U.S. Application Data

(63) Continuation of application No. PCT/US2012/070173, filed on Dec. 17, 2012.

(60) Provisional application No. 61/576,721, filed on Dec. 16, 2011.

(51) Int. Cl.
| | | |
|---|---|---|
| A61K 9/00 | (2006.01) | |
| A61L 27/52 | (2006.01) | |
| A61L 27/38 | (2006.01) | |
| A61L 27/26 | (2006.01) | |
| A61L 27/54 | (2006.01) | |
| A61L 27/48 | (2006.01) | |

(52) U.S. Cl.
CPC ............... *A61L 27/54* (2013.01); *A61L 27/26* (2013.01); *A61L 27/38* (2013.01); *A61L 27/3813* (2013.01); *A61L 27/48* (2013.01); *A61L 27/52* (2013.01); *A61L 2430/34* (2013.01)

(58) Field of Classification Search
CPC .......... A61L 27/54; A61L 27/26; A61L 27/38; A61L 27/3813; A61L 27/48; A61L 27/52
See application file for complete search history.

(56) References Cited

U.S. PATENT DOCUMENTS

2007/0286885 A1* 12/2007 Hossainy ............... A61K 38/08
                                                                                 424/426
2010/0291045 A1* 11/2010 Jia .......................... C12M 21/08
                                                                                 424/93.7

OTHER PUBLICATIONS

Pradhan et al., Lumen formation in three-dimensional cultures of salivary acinar cells. Otolaryngology—Head and Neck Surgery, vol. 142 (2010) pp. 191-195.*

* cited by examiner

*Primary Examiner* — Kara Johnson
(74) *Attorney, Agent, or Firm* — Reed Smith LLP; Robert R. Riddle; Matthew S. Gibson

(57) ABSTRACT

Implantable modular hydrogels to aid in salivary gland restoration and associated methods are provided. In one embodiment, the present disclosure provides for a hydrogel network comprising: a hyaluronic acid macromer cross-linked with a multiblock copolymer.

22 Claims, 19 Drawing Sheets
(14 of 19 Drawing Sheet(s) Filed in Color)

Acrylated HA (HA-AC)

Error bars=SEM, n=12, ***p<0.001 compared to control.

Treatment (1hr)

Error bars=SEM, n=8, *p<0.05 compared to control.

`US 9,642,941 B2`

IMPLANTABLE MODULAR HYDROGEL FOR SALIVARY GLAND RESTORATION

CROSS-REFERENCE TO RELATED APPLICATIONS

The present application is a continuation of PCT/US12/70173, filed Dec. 17, 2012 which claims priority to U.S. Provisional Patent Application Ser. No. 61/576,721 filed Dec. 16, 2011 which is incorporated herein by reference.

STATEMENT REGARDING FEDERALLY SPONSORED RESEARCH OR DEVELOPMENT

This invention was made with government support under Grant No. 1R01DE022969-01 awarded by National Institute of Health. The government has certain rights in the invention.

BACKGROUND

Saliva is an essential oral lubricant containing an array of vital proteins for maintaining oral health. Head and neck cancers account for 3% of all malignancies in the United States. Dry mouth due to significant decreases in saliva secretion (xerostomia) is a permanent and devastating side effect of head and neck radiation that affects approximately 40,000 patients a year in the U.S. Radiation treatment (RT) preferentially damages secretory acinar cells, resulting in a near-complete loss of saliva, a dramatic increase in tooth decay, difficulty in swallowing, and other issues. Radiation treatment in patients with head and neck tumors commonly results in hyposalivation and xerostomia due to the loss of fluid secreting salivary acinar cells. Patients develop susceptibility to oral infections, dental caries, impaired speech and swallowing, reducing the quality of life.

Clinical management is largely unsatisfactory. Current prevention methods (e.g. radioprotective agents or highly localized intensity modulated RT) are generally ineffective. Although advanced radiation techniques such as Intensity-Modulated Radiation Therapy (IMRT) significantly reduce radiation to the salivary glands compared to conventional radiation, a large percentage of patients develop xerostomia post-IMRT. Post-radiotherapy palliative therapies remain largely ineffective for long-term resolution of xerostomia. Other xerostomia treatments, such as artificial saliva or stimulatory agonists, are also largely ineffective. Tissue engineering offers a potential safe clinical solution for the regeneration of tissue and recovery of salivary function.

Recent clinical success in tissue engineering includes tissues such as cartilage, bone and bladder. U.S. Pat. Nos. 7,803,905 and 7,875,591, the entireties of which are hereby incorporated by reference, discuss methods of adhering cells to scaffolds and devices to induce replication of connective tissues. Functional reconstitution of a 3D glandular structure such as the human salivary gland is difficult, owing to a complex tissue structure of distinct cell types that must reassemble to provide vectorial secretion of a complex biological fluid. Despite extensive recent research in salivary gland development, efforts at regeneration using the classic tissue engineering models are few, and suffer from insufficient sources of cells and scaffold materials. Synthetic scaffolds, such as PGA/PLLA lack necessary cues, have inappropriate mechanical properties, and produce potentially inflammatory degradation byproducts. Collagen/matrigel hybrids are closer matches to native tissue, both in gel modulus and composition, but murine Matrigel cannot be used for human repair. Recent work suggests that well-defined polysaccharide gels may be a potential solution. Cell sourcing remains a substantial obstacle, with researchers reporting difficulties in reliably isolating and expanding human acinar, ductal, and myoepithelial cells (MECs).

SUMMARY

The present disclosure generally relates to salivary gland restoration. More particularly, the present disclosure relates to implantable modular hydrogels to aid in salivary gland restoration and associated methods.

In certain embodiments, the present disclosure provides a hydrogel network comprising: a hyaluronic acid macromer crosslinked with a multiblock copolymer.

In certain embodiments, the present disclosure provides a kit comprising a hyaluronic acid macromer and a multiblock copolymer.

In certain embodiments, the present disclosure provides a method of forming a hydrogel network comprising: providing a hyaluronic acid macromer; providing a multiblock copolymer, and crosslinking the hyaluronic acid macromer with the multiblock copolymer to form the hydrogel network.

In certain embodiments, the present disclosure provides a method of constructing a biomimetic matrix comprising: providing a hyaluronic acid hydrogel network, providing hyaluronic acid hydrogel particles, providing salivary cells, and co-encapsulating the hyaluronic acid hydrogel particles and the salivary cells within the hyaluronic acid hydrogel network to form cell-laden microgel modules.

In certain embodiments, the present disclosure provides a composition comprising: a hyaluronic acid macromer; a multiblock copolymer comprising a copolymer of PlnDIV peptide alternating with PEG; and hyaluronic acid hydrogel particles.

The features and advantages of the present disclosure will be apparent to those skilled in the art. While numerous changes may be made by those skilled in the art, such changes are within the spirit of the invention.

DRAWINGS

The patent or application file contains at least one drawing executed in color. Copies of this patent or patent application publication with color drawings will be provided by the office upon request and payment of the necessary fee.

Some specific example embodiments of the disclosure may be understood by referring, in part, to the following description and the accompanying drawings.

FIG. 1 is drawing that illustrates a strategy for creating salivary cell modules. Strategy for creating salivary cell modules. GF-loaded HGPs will be co-encapsulated within an HA matrix, crosslinked by a PlnDIV-PEG copolymer to produce microscale Cell-MMs. Multiple Cell-MMs will then be gelled with angiogenic HGPs to produce a 3D-ST implant.

FIG. 2 is a drawing that illustrates a research strategy for Cell-MM formation. Cell-MM formation allows many versatile combinations of materials and cells to be included. Salivary cells will be cultured in HA hydrogels, with GF-loaded HGPs to enhance cell growth and progenitor character, optimize lumen formation via [PlnDIV-PEG], induce acinus extension and/or branching via FGF7/10 gradients and stabilize structures via MEC support.

FIG. 3 is a drawing that illustrates a strategy for design and in vivo testing of various 3D-ST composite constructs.

HGPs and MMs can be encapsulated in HA to assess the following points: using VEGF/FGF2 HGPs alone in HA to optimize angiogenesis, adding cell-free MMs to confirm neovessel access to MMs, confirming acinar-enriched cell assembly in cell-MMs in vivo and determining the need for MECs in fully-assembled 3D-STs.

FIG. 4 illustrates HGP images. (a) Scanning electron micrograph (SEM) of 10 μm HGPs; (b) diagram of HBGF binding to PlnDI(HS) or heparin throughout the porous HGP (c) cryogenic SEM image of HA DXN FIG. 5 is a drawing that illustrates multiblock [PlnDIV-PEG]n copolymer crosslinkers. Multiblock [PlnDIV-PEG]n copolymer crosslinkers [PlnDIV-PEG]n are synthesized by step growth polymerization via orthogonal CuAAC click chemistry FIG. 6 is a schematic of HA carrying unsaturated double bonds (HA-AC). n=0-3.

FIG. 7 is a chart depicting the relationship between cumulative release and time. GF release kinetics from HGPs, functionalized with low (HP1) or high (HP10, HP100) levels of heparin. GF release can be tuned to vary inversely with HP content.

FIG. 8 is a chart that illustrates a method for making cell-MMS. Microfabrication method to make cell-MMs. (a) Laser-cut patterns in PDMS with varying xy features; (b) SEM of 1 mm well in a PDMS template; (c) multiple HA hydrogel discs from circular templates; (d) 3D confocal image of bilayers in (c), using covalently-bound fluors. Scale bar=4 mm FIG. 9 is a picture that illustrates human salivary-derived cells in 2D culture. (a,b) acinar cells, >99% $CK5^+$ and $\beta$-amylase$^+$; (c) co-culture of ductal cells (CK19+, red) and acinar cells; (d) myoepithelial cells (MECs).

Figure 16:
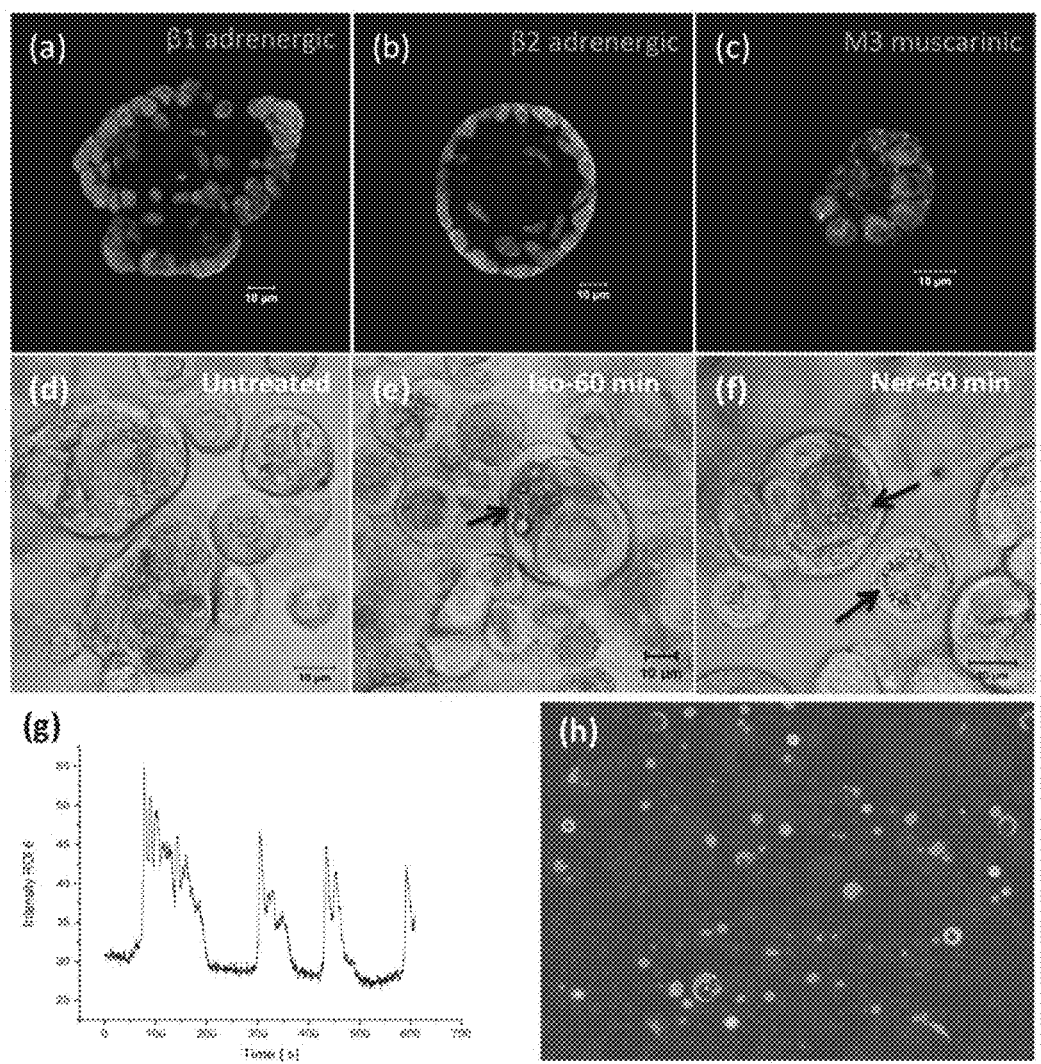

FIG. 16 illustrates the response of spheroids in HA to neurotransmitters. (a-c) Expression of adrenergic/muscarinic receptors in spheroids; (d-f) Spheroid response to isoproterenol or norepinephrine, demonstrating peripheral granule formation and concentrated β-amylase over untreated control (d); Arrows point to granules; (g-h) $Ca^{2+}$ spikes in spheroids in response to ACh treatment, observed by Fluo-4 imaging. (g) confocal line scan intensity; (h) sample image.

Figure 17:
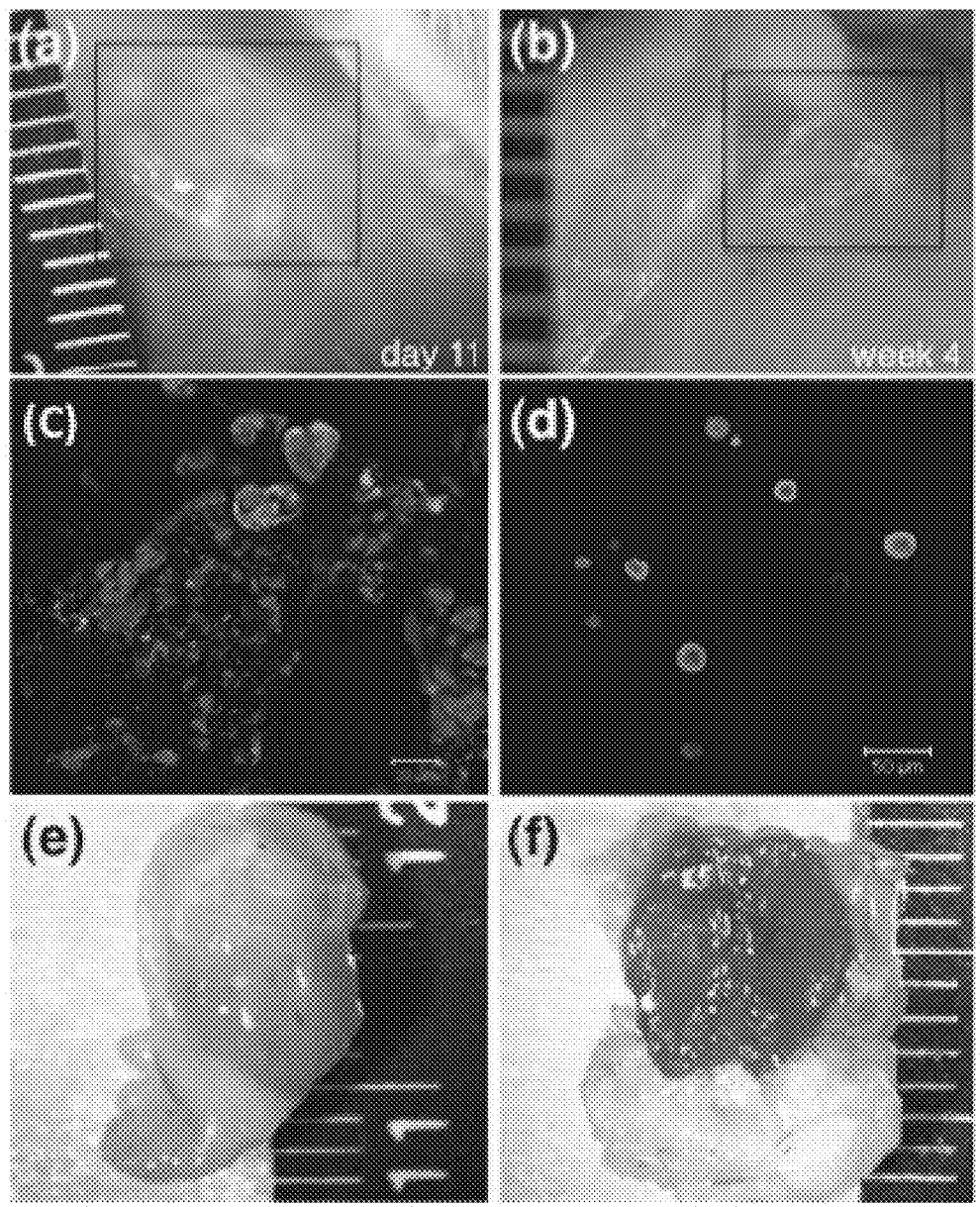

FIG. 17 illustrates the biocompatibility of HA hydrogels in nude rat. Bare HA hydrogel after (a) 11 d, (b) 4 w of implantation. (c.d) Cell-loaded implants maintain cells in spheroids (boxed) in vivo in the back (c) and parotid bed (d). Cells express β-amylase (red) and cytokeratins (green). HA hydrogels with empty HGPs (e) and VEGF-loaded HGPs (f) after 1 w in parotid bed. The intense red color (f) is due to increased vascularization over control (e).

Figure 18:
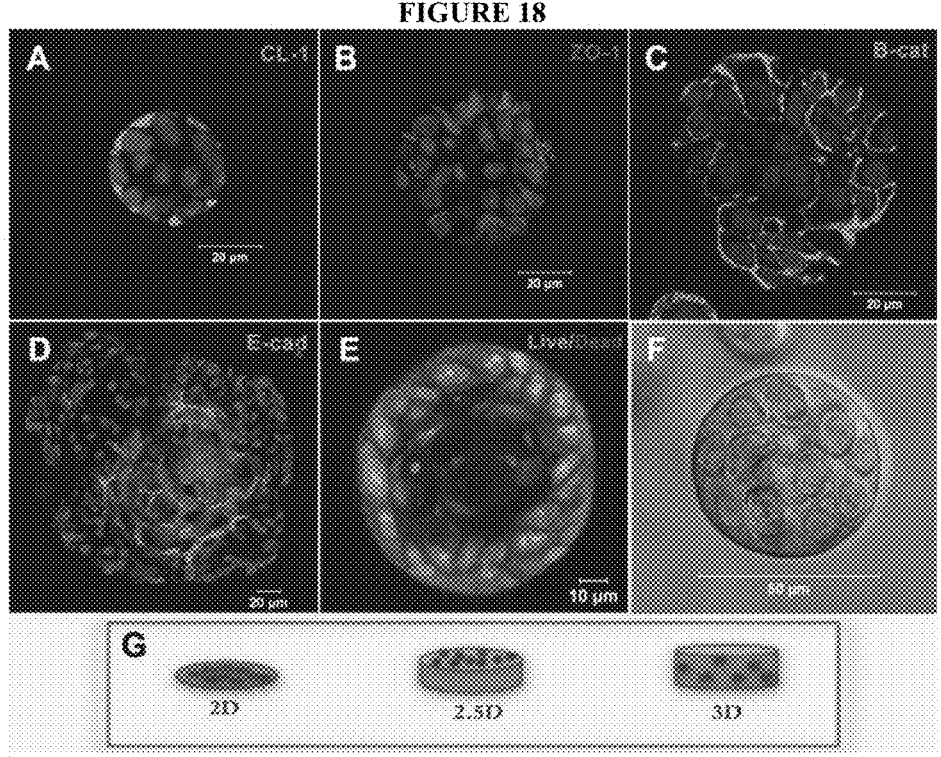

FIG. 18 shows Acini-like spheroids in 3D HA hydrogels. Spheroid structures express tight junction markers CL-1 (A), ZO-1 (B), E-cadherin (D) and adherens junction marker, β-catenin (C). Live/Dead staining shows Syto13 positive green cells and propidium iodide positive red cells (E). A representative phase image of an acinus-like structure is seen in F. Nuclei stain blue. An illustration of hydrogel dimensionality is seen in G.

Figure 19:
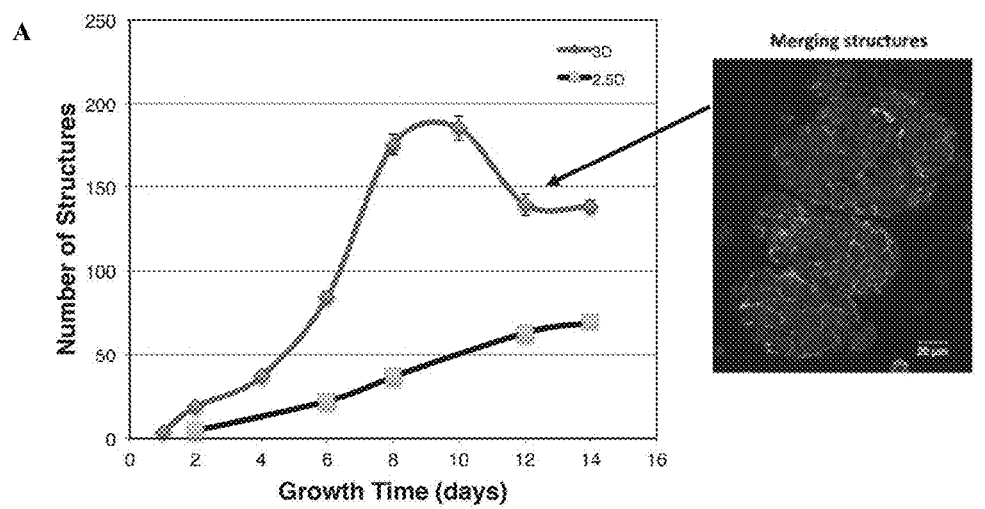
Figure 19:
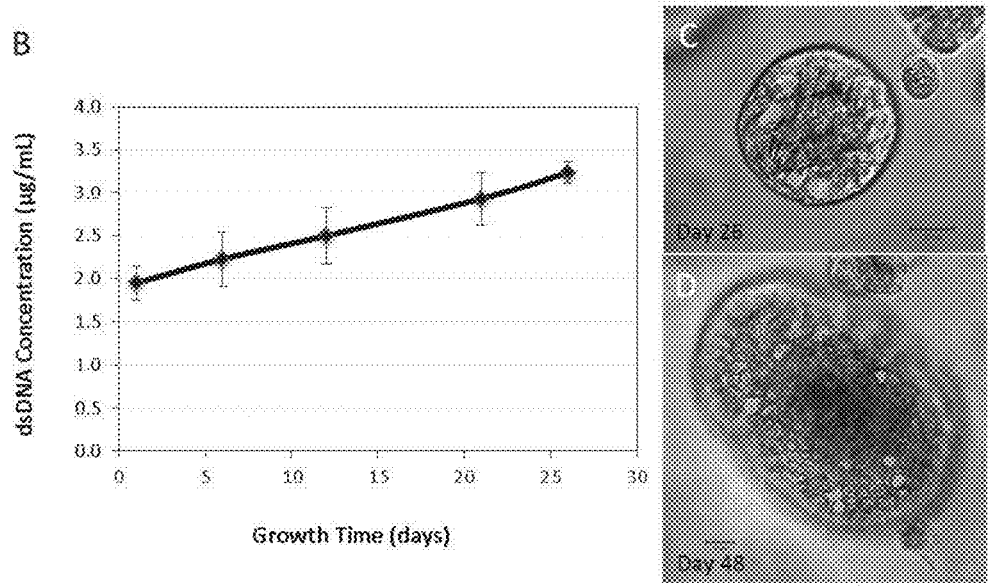

FIG. 19 shows (A) Differences in growth of acini-like structures in 2.5D (red) and 3D (blue) HA hydrogels. (B) Quantification of dsDNA in acini-like structures growing in 3D HA hydrogels. Each point represents the average of n=3 measurements. Error bars are +/− standard error. (C) and (D) show Ki67 staining (green) in acini-like structures at day 26 (C) and at day 48 (D).

Figure 20:
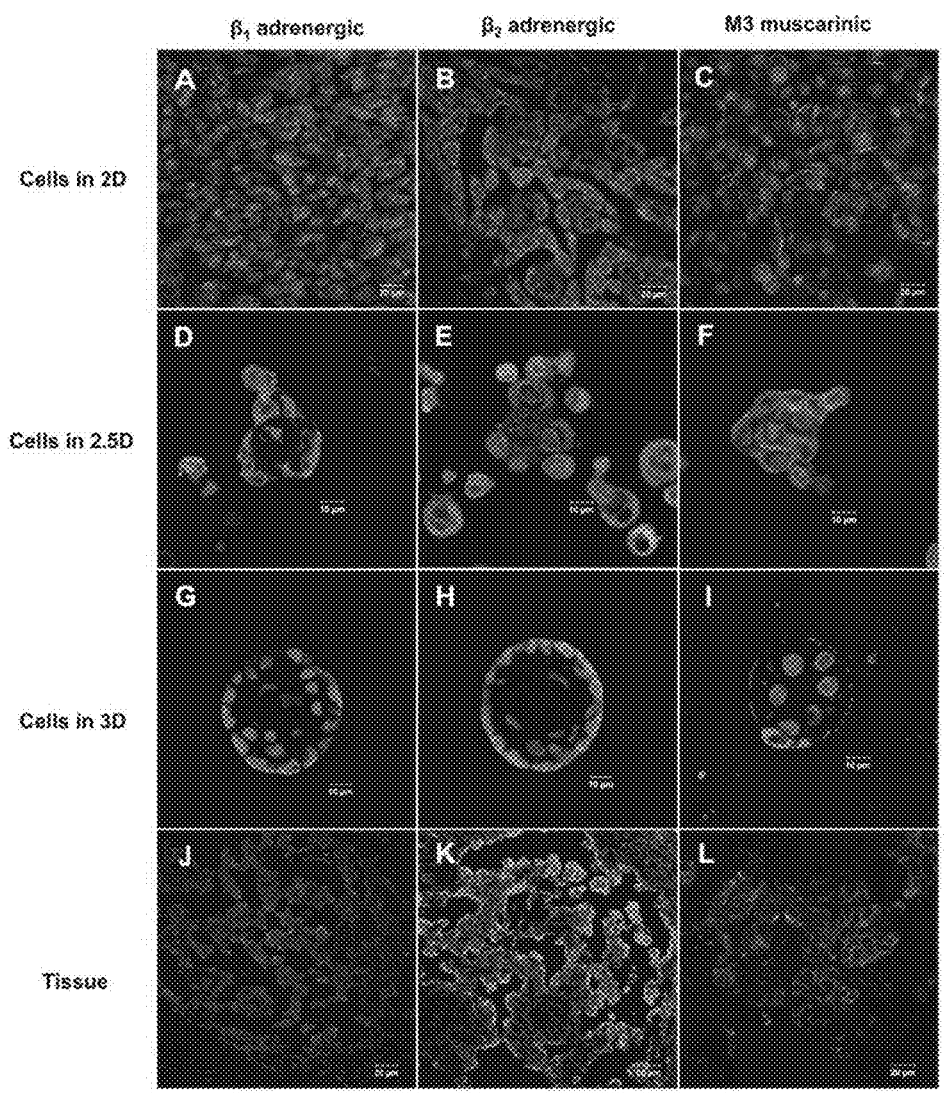

FIG. 20 shows salivary acinar-like cell assemblies express receptors for neurotransmitters. Confocal images show expression of β1 adrenergic receptor (A, D, G, J), 2 adrenergic receptor (B, E, H, K), and M3 muscarinic receptor (C, F, I, L) in 2D cultured cells (A-C), on 2.5D HA hydrogels (D-F), in 3D hydrogels (G-I) and in tissue (J-L). Nuclei stain red.

Figure 21:
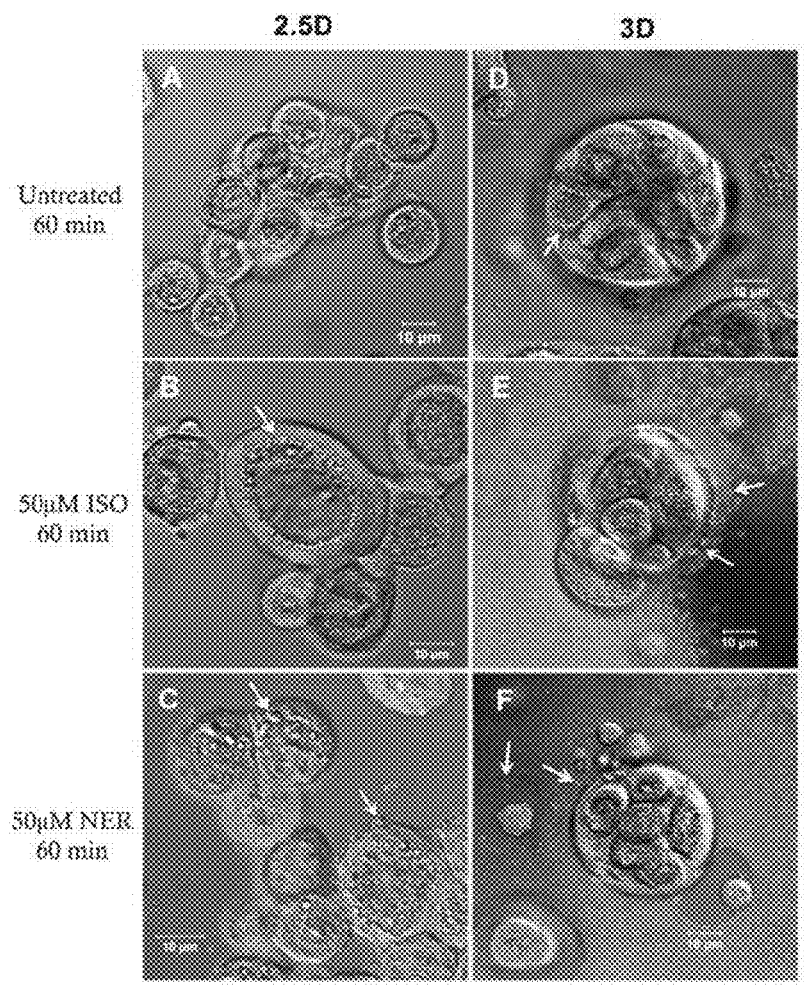

FIG. 21 shows salivary acinar-like cell assemblies in 2.5D and 3D HA hydrogels form secretory granules upon treatment with isoproterenol (ISO) and norepinephrine (NER). Images captured with the confocal microscope using brightfield and fluorescence. Panels A-C show cells on 2.5D hydrogels while panels D-F show cells encapsulated in 3D hydrogels. Control untreated cells are shown in panels A and D. Cells treated with 50 μM ISO for 60 minutes (B, E) show presence of granules (arrows). Cells treated with 50 μM NER for 60 minutes (C, F) also show granule production. α-Amylase is stained red.

Figure 22:
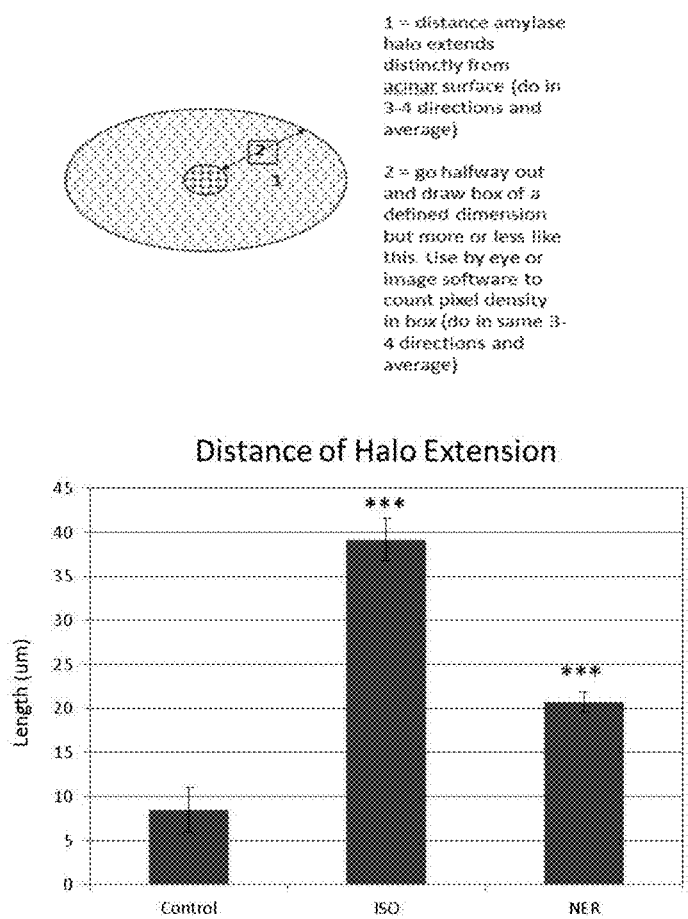

FIG. 22 demonstrates the distance of α-amylase release from each acini, as measured from fluorescence staining for α-amylase. As seen in the measurements, acini are responsive to ISO and NER, since these two agents induce a further distance of α-amylase release. α-amylase production is visible as a halo surrounding the cells in 3D culture.

Figure 23:
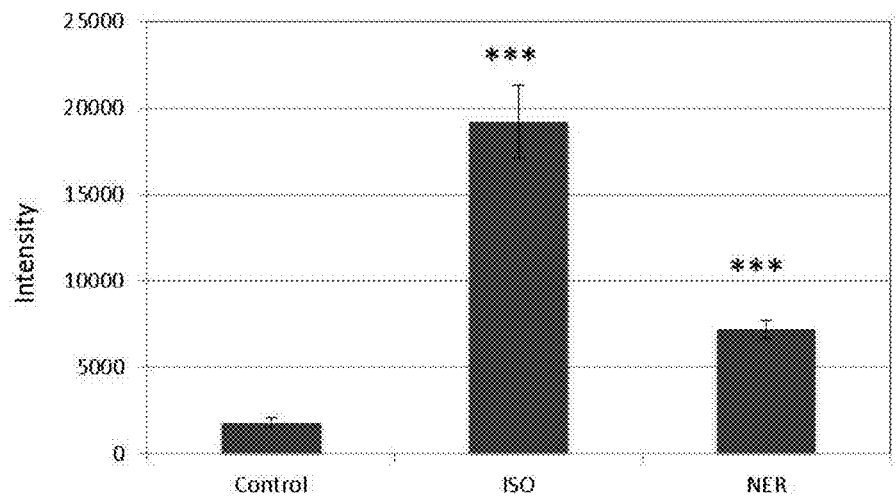

FIG. 23 is a complementary measure of α-amylase response, using an integrated intensity of the antibody fluorescence over a selected area to demonstrate α-amylase release in response to ISO and NER agents.

Figure 24:
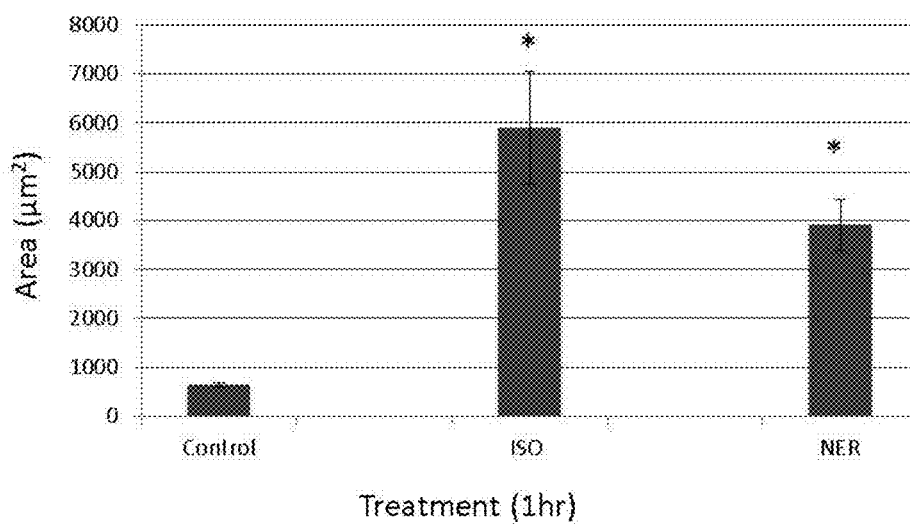

FIG. 24 shows and establishes the area of identified α-amylase response around each cell assembly. The increase in area for ISO and NER-treated assemblies confirms their responsiveness to these two agents.

Figure 25:
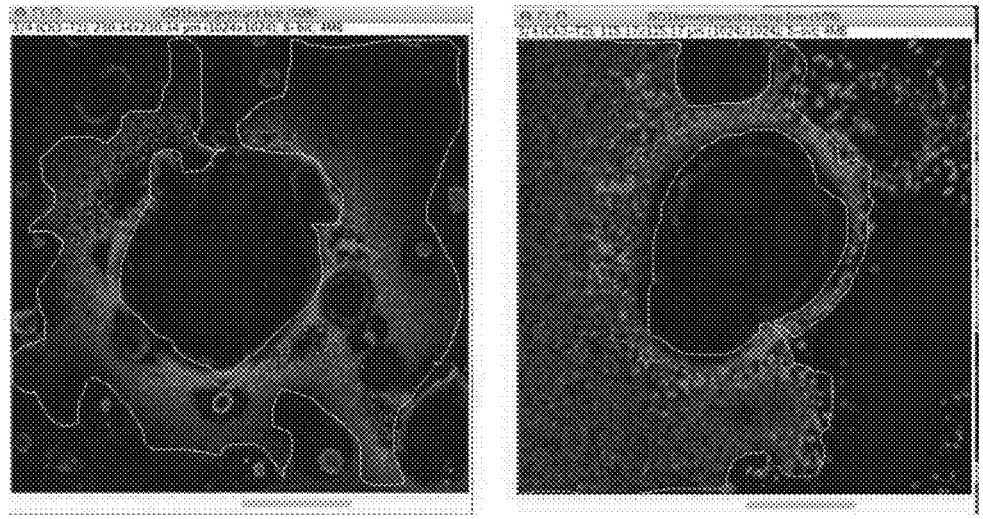

FIG. 25 shows amylase production for cells treated with ISO. α-Amylase is stained red. The outlined region of interest was used for quantification of α-amylase response.

Figure 26:
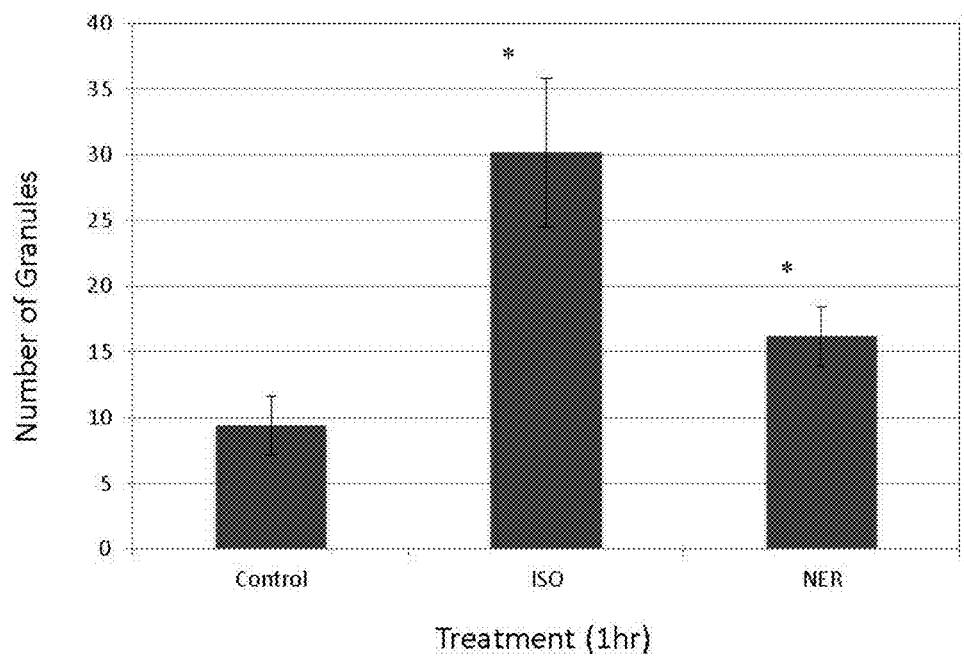

FIG. 26 shows the number of secretory granules of cell assemblies after treatment with isoproterenol (ISO) and norepinephrine (NER) as compared to controls.

Figure 27:
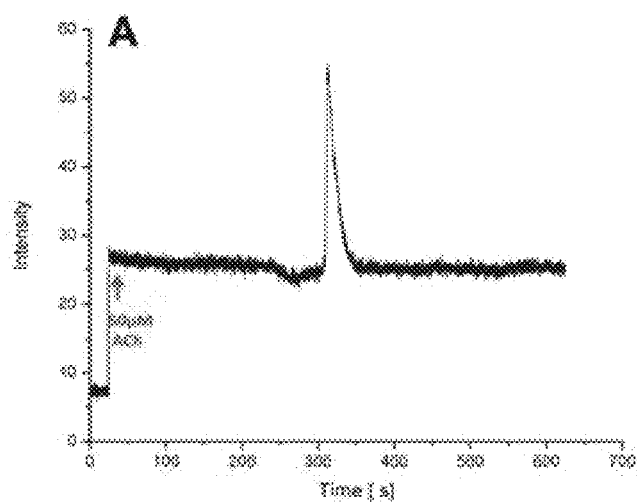
Figure 27:
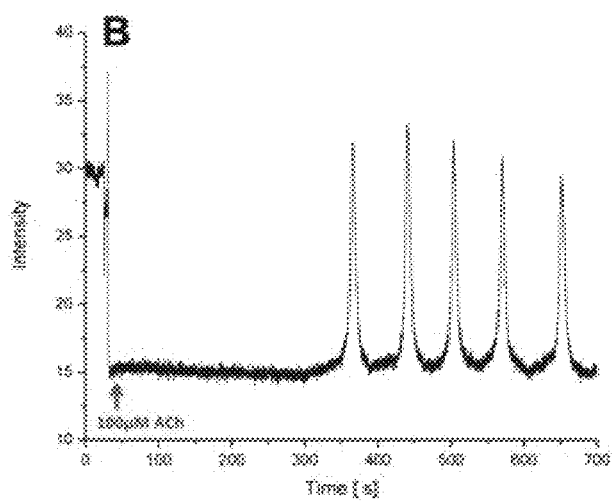
Figure 27:
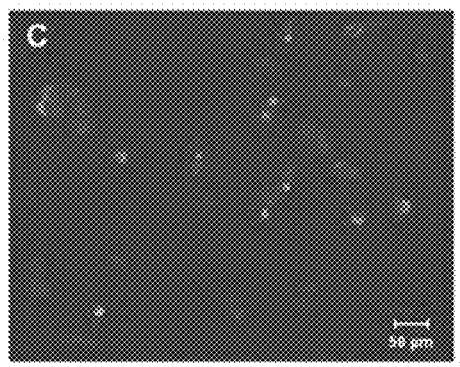
Figure 27:
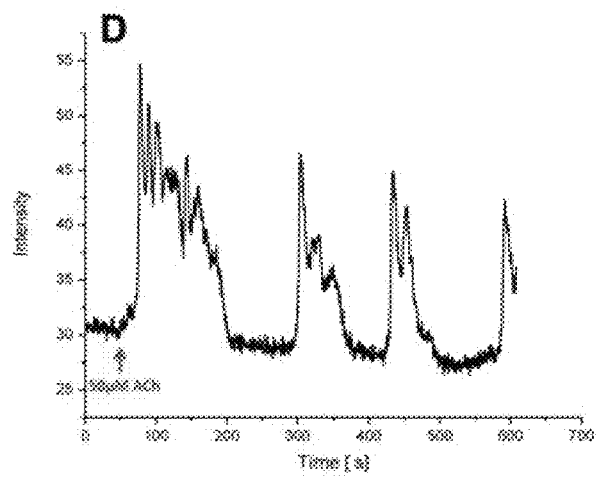
Figure 27:
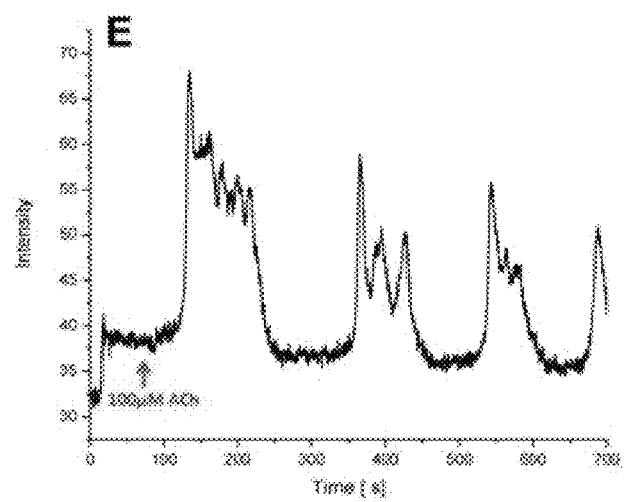
Figure 27:
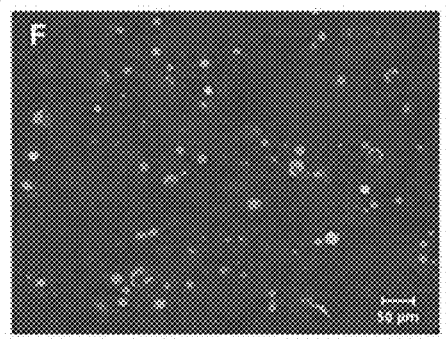

FIG. 27 illustrates that acetylcholine induces intracellular calcium release in self-assembling acini-like structures cultured on HA hydrogels. Intracellular calcium is released from the ER stores upon activation of M3 muscarinic receptors. Calcium curves generated from cells on 2.5D hydrogels (A), and oscillations from cells in 3D hydrogels (D), upon treatment with 50 μM acetylcholine. Calcium oscillations generated upon treatment with 100 M acetylcholine in cells in 2.5D (B) and in 3D (E). Red arrow indicates the time-point at which acetylcholine was added. Representative images of structures in 2.5D (C) and in 3D (F) responding to acetylcholine are seen in a rainbow/heat map scale where red indicates the highest response and blue indicates the lowest or no response.

Figure 28:
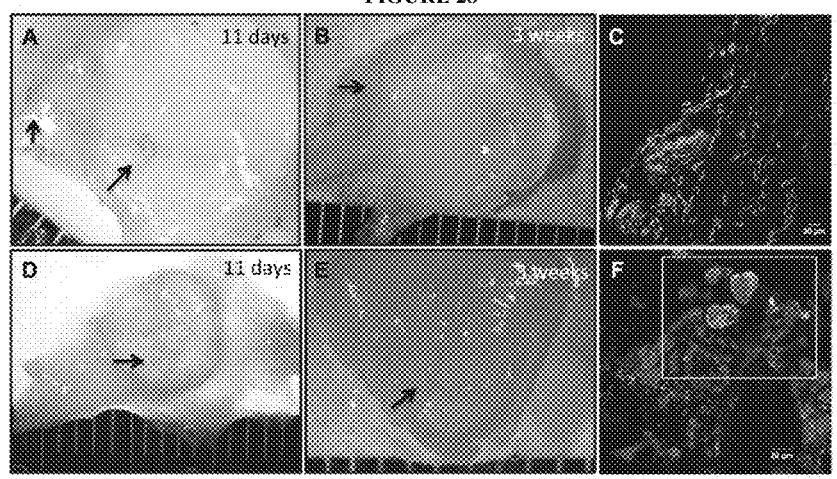

FIG. 28 shows survival and retention of acini-like structures in 2.5D and 3D hydrogels. 2.5D implants wrapped in gelatin membranes removed from athymic rats at day 11 (A) and at 3 weeks (B). 3D implants removed from athymic rats at day 11 (D) and at 3 weeks (E). Dispersed single cells positive for α-amylase (red) in rat tissue stained with vimentin (green) are seen in panel C. Intact spheroid structures (boxed) in the 3D hydrogel implant stained for α-amylase (red) and β-catenin (green) are seen in panel F. Arrows point to blood vessels.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to salivary gland restoration. More particularly, the present disclosure relates to implantable modular hydrogels for salivary gland restoration and associated methods.

Salivary tissue engineering potentially offers permanent relief of xerostomia. The autonomic nervous system innervates salivary acinar, myoepithelial, vascular and intercalated duct cells. Salivary acinar cells secrete most of the fluid, electrolyte and proteins in saliva. Neurotransmitter receptors are present on the basolateral membranes of acinar cells that possess α-adrenergic, β-adrenergic, M3 muscarinic, and cholinergic substance P receptors.[3] The major pathway for protein exocytosis occurs via activation of β-adrenergic receptors (sympathetic pathway), while the primary stimulation for fluid secretion occurs through activation of the M3 muscarinic receptors (parasympathetic pathway).

The most abundant protein in saliva, α-amylase, comprises 10% of all salivary protein and is actively secreted by stimulated acinar cells. Secreted salivary proteins such as α-amylase are stored at high concentrations in specialized secretory granules. Two distinct pathways regulate trafficking of secreted and ECM proteins. Several are secreted by a constitutive pathway that allows for exocytosis of secreted proteins without stimulation. However, exocytosis can be regulated for controlled release of granule contents. The regulated secretory pathway is the major pathway for granule exocytosis. In this pathway, neurotransmitter agonists such as norepinephrine bind to G-protein coupled β-adrenergic receptors that, in turn, activate the adenyl cyclase/cAMP/Protein Kinase A (PKA) second messenger pathway to stimulate protein exocytosis.

Transport of fluid also occurs in two distinct ways among glandular epithelia. Fluid can move through the plasma membranes via transcellular transport or through the tight junctional barrier via paracellular transport. Studies with rat and rabbit submandibular glands showed that most fluid is transported via the paracellular pathway with less transported via the transcellular pathway. The transepithelial movement of water via the paracellular pathway is the primary mechanism for fluid secretion by salivary acinar cells.

Fluid secretion can be activated by binding of acetylcholine to M3 muscarinic receptors, and subsequent activation of G proteins. The α-component of the G protein then dissociates and activates phospholipase C (PLC), forming inositol triphosphate ($IP_3$) and releasing calcium from intracellular stores. Calcium then activates the apical calcium activated chloride channels. As chloride is released into the lumen, sodium from the interstitium follows. The resulting sodium chloride creates an osmotic gradient that drives transepithelial movement of water into the lumen.

The present disclosure describes an implantable, biologically-based cell-seeded 3D implant that will aid in restoring salivary function in patients suffering from xerostomia.

Figure 1:
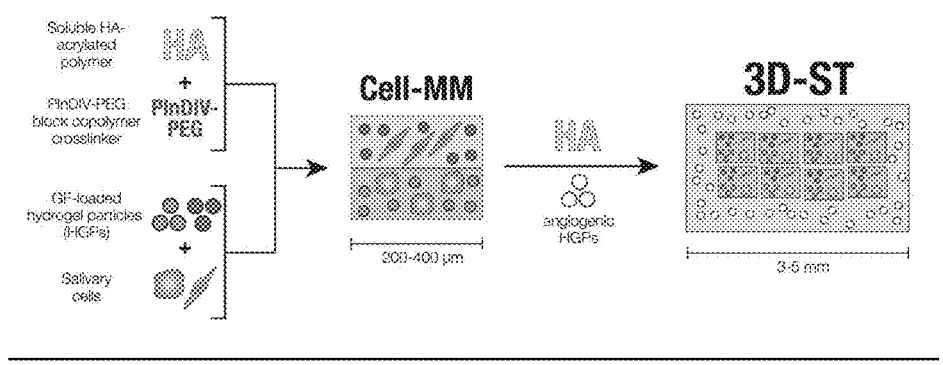

The present disclosure also describes a novel modular approach for the creation of functional salivary cell hydrogel assemblies (cell-MMs) that can be co-assembled into a larger 3D-ST (3D salivary neotissue) hydrogel for direct implantation into patients. FIG. 1 illustrates such an approach. Specifically, biomimetic matrices providing defined biological cues can be constructed from these building blocks: (1) chemically modified hyaluronic acid (HA) with reactive handles; (2) multiblock copolymer crosslinkers, and (3) microscale densely crosslinked HA-based hydrogel particles (HGPs), which serve as depots for growth factors (GF). HGPs (pre-loaded with selected GFs) and salivary cells may be co-encapsulated within an HA hydrogel network to form cell-laden microgel modules (cell-MM). Cell-MMs may be the primary modular building blocks for this device. Additional complexity may be built by gelling multiple cell-MMs into a secondary HA network, yielding a larger, macroscopic 3D-ST construct for final implantation. The modular building blocks, when combined with the salivary cellular components, may create a new solution for patients suffering from xerostomia.

Figure 6:
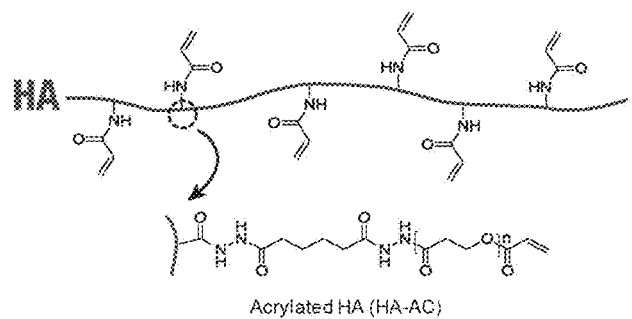

In one embodiment, the present disclosure provides for a hydrogel network comprising: a hyaluronic acid (HA) macromer crosslinked with a multiblock copolymer. HA is a naturally-derived, biocompatible matrix that can be chemically functionalized for use as a crosslinkable tissue engineering scaffold. Unlike other hydrogels, HA is uniquely recognized by cellular receptors, in particular CD44, ICAM-1 and RHAMM. HA is a ubiquitous polysaccharide found throughout the ECM, and unlike poly(ethylene glycol) (PEG) and other hydrogels, it binds specific receptors (CD44, RHAMM, ICAM-1), which are expressed on salivary gland cells, and direct multiple cell functions including adhesion, migration, and morphogenesis. HA derivatives with reactive handles can be used for in situ cell encapsulation for 3D culture purposes. The HA may be functionalized with any group that would allow for it to be crosslinked with a multiblock copolymer. In certain embodiments, the HA may be functionalized with an unsaturated double bond (FIG. 6). In certain embodiments, the HA may be functionalized with an acrylate group. The hydrogel network of the present disclosure may be biocompatible.

The multi-block copolymer of the present disclosure may comprise an alternating copolymer of PEG and a peptide epitope of perlecan. Cell-instructive biological cues may be incorporated into the HA networks using the novel multiblock alternating copolymer of PEG and a peptide epitope from perlecan. Perlecan (Pln) is a proteoglycan present in all basement membranes where it serves as both a structural boundary marker and as a reservoir for heparan sulfate/heparin (HS/HP) binding growth factors (HBGFs). Pln offers a novel alternative for tissue engineering applications compared to other biologicals (e.g. collagen, fibronectin, laminin, Matrigel). In certain embodiments, two specific segments of Pln may be employed: (a) Domain I of Pln (PlnDI) includes three polysaccharide chains of predominantly heparan sulfate, which bind HBGFs in native tissue, and which will be used here (as a depot for delivery of multiple relevant GFs; (b) Within Pln Domain IV, a 17-mer sequence (PlnDIV peptide) interacts preferentially with epithelial cells, which may be used to influence salivary cell organization. U.S. Pat. No. 7,875,591 describes delivery systems for heparin-binding growth factors, the disclosure of which is herein incorporated by reference.

In certain embodiments, PlnDIV peptide may be used in the multiblock PEG copolymers described above. U.S. Pat. No. 7,803,905 describes the perlecan domain IV peptide, the disclosure of which is herein incorporated by reference. In certain embodiments, [PlnDIV-PEG]$_n$ copolymers may provide additional cellular cues in the HA matrix, amplified through multivalency to elicit coordinated and dynamic cell-matrix interactions. Michael-type addition reactions may be employed between sulfhydryl groups on the [PlnDIV-PEG]$_n$ copolymer and reactive double bonds on HA to form the secondary network. This reaction occurs rapidly at pH 7, resulting in a thioether bond with no toxic byproducts. Hydrogel stability can be tuned by varying the neighboring groups to the thioether.

In certain embodiments, [PlnDIV-PEG]$_n$ multiblock copolymers may be synthesized via condensation polymerization using copper(I)-catalyzed alkyne-azide cycloaddition reaction (CuAAC). Azide-terminated, telechelic PEG with $M_n$ of 400, 1,450, 3,400 and 5,000 may be synthesized and purified. PlnDIV peptide may be tagged with the non-natural amino acid, propargyl glycine, to facilitate CuAAC coupling between peptide and α,ω-azido PEG. The functional group tolerance of CuAAC and the modular nature of the synthesis permit ready adjustment of the composition of the multiblock.

In certain embodiments, the multiblock copolymer comprises a multiblock alternating copolymer of poly(acrylic acid) (PAA) and a hydrophobic peptide with a sequence of (VPGVG)$_2$. In certain embodiments, a combination of multiblock copolymers may be used in the hydrogel network. For example, in certain embodiments, a combination of a multiblock copolymers comprising a multiblock alternating copolymer of poly(acrylic acid) (PAA) and a hydrophobic peptide with a sequence of (VPGVG)$_2$ may be combined with a multiblock copolymer [PlnDIV-PEG]$_n$.

In certain embodiments, to render the multiblock copolymers crosslinkable towards HA derivatives carrying an unsaturated double bond (FIG. 6), a cysteine residue may be added to the basic peptide sequence. The peptide motifs may be X(PlnDIV)XGGC, where PlnDIV will have a sequence of TWSKVGGHLRPGIVQSG, X is propargyl glycine, G is a gly spacer and C is a cys tag. Peptides may be prepared by solid phase peptide synthesis and purified. The [PlnDIV-PEG]$_n$ products may be purified and characterized by standard means. Filtration through Cuprisorb resin and dialysis against thiourea, imidazole, NaCl, and pure water solutions may yield polymers that are non-toxic to cells.

In certain embodiments, cells may be encapsulated within the hydrogel network. In certain embodiments, the cells may be any cells or combinations of cells derived from the salivary gland, including but not limited to stromal, epithelial, myoepithelial, ductal, and nerve cells. In certain embodiments, the cells may be salivary cells. In certain embodiments, the cells may be parotid gland derived cells. In certain embodiments, the cells may be salivary gland progenitor cells. In certain embodiments, the cells may be salivary acinar-like cells. In certain embodiments, the cells may be included in the hydrogel network in an amount ranging from about $1 \times 10^5$ cells/200 µL volume of hydrogel to about $1 \times 10^7$ cells/200 µL volume of hydrogel. The amount of cells included in the hydrogel network will depend on the specific cell type and desired application. In certain embodiments, the cells may be treated with β-adrenergic agonists. In certain embodiments, the cells may be treated with M3 muscarinic agonists. In certain embodiments, the cells may be treated with norepinephrine, isoproterenol, acetylcholine, and combinations thereof. In certain embodiments, β-adrenergic agonists, M3 muscarinic agonists, norepinephrine, isoproterenol, and acetylcholine may be delivered to cells using HA-based hydrogel particles.

Figure 4:
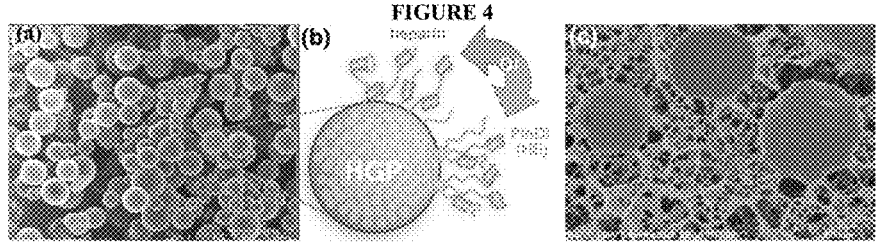
Figure 5:
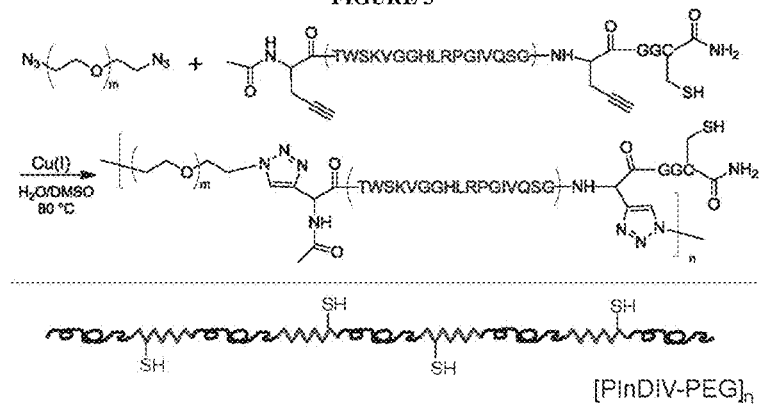

In certain embodiments, HA-based hydrogel particles (HGP) may also be included in the hydrogel network. In certain embodiments, HGPs may be included in the hydrogel network in an amount of from about $1 \times 10^4$ to $1 \times 10^6$ HGPs per hydrogel network, however the amount of HGPs can be tailored depending on the specific application. In certain embodiments, HGPs may provide local growth factor stores to induce programmed morphogenesis. The HGPs can be tailored to provide various amounts of growth factor depending on the application. In certain embodiments, the HGPs may be angiogenic HGPs. In certain embodiments, HGPs of micro- to nano-dimensions may be embedded within porous HA hydrogel matrices (FIG. 4). In certain embodiments, the HGPs may be spherical. In certain embodiments, the spheres may have a diameter in the range of from about 500 nm to about 10 µm. HGPs may be chemically functionalized to crosslink with both the HA hydrogel matrix, and with other HGPs, enabling tailored viscoelasticity, enzymatic stability and structural integrity, essential for tissue regeneration. These properties can be easily tuned by varying the size and number of HGPs, the crosslinking chemistry, and the density of the primary and the secondary networks. HGPs may also deliver and release therapeutic GFs at targeted locations and controlled rates (FIG. 7) to elicit desired cellular behavior. In certain embodiments, HGPs may be co-encapsulated, and may release HBGFs sequentially in a controlled manner to induce cellular differentiation and tissue morphogenesis in situ. The modular nature of the building blocks allows for fine-tuning of the biological and biomechanical properties of the resulting matrix.

Salivary gland morphogenesis and angiogenesis require coordination among multiple GFs, including HB-EGF, FGF2, FGF7, FGF10 and VEGF. The hydrogel network of the present disclosure may comprise local GF stores capable of controlled delivery. For example, covalently immobilized PlnDI(HS) or heparin (HP) on HGPs may be used for the non-covalent association of the HBGFs, allowing HBGFs to form latent complexes through their specific binding. Such strategies offer the potential for sustained release over timescales relevant to controlling the initial cellular assembly in vitro and subsequent angiogenesis of the neotissue in vivo. It has been shown that HGPs, covalently functionalized with PlnDI(HS), can sequester BMP-2, modulate its release, and potentiate its biological functions, both in vitro and in vivo. Similar sustained release of BMP-2 may be achieved using HGPs with covalently integrated HP (see FIG. 7).

Covalently immobilized PlnDI(HS) or HP may be used for non-covalent GF association. Sequential GF release may be achieved by tailoring GF affinity for HGPs via the variation of HS/HP content in the particles. When HS/HP content is high, GF release is slow, as locally dissociated proteins are rapidly recaptured by unoccupied HS/HP sites before they can diffuse into the surrounding medium. When HS/HP content is low, GF is rapidly released through diffusion. It has been demonstrated that controlled BMP-2 release by HA/HP hybrid particles, along with the innate bioactivity of HA, induced robust and consistent chondrogenic differentiation of mesenchymal stem cells. The relative amount of HP incorporated in HGPs may be easily tuned by varying the HA/HP ratio in feed during particle synthesis.

In certain embodiments, multiple hydrogel networks can be co-assembled to form a secondary hydrogel network. The secondary network may be a larger 3D assembly or construct that may be implanted into a subject. In certain embodiments, the secondary network may be formed by coassembly individual hydrogel networks with hyaluronic acid and HA hydrogel particles. In certain embodiments, the HA hydrogel particles may comprise angiogenic HGPs.

Under this autologous restoration paradigm, the salivary gland progenitor cells may be isolated prior to radiation treatment, expanded and/or manipulated in vitro, and returned to the site of injury via a biocompatible implant. Salivary gland regeneration is particularly challenging, as the gland is a complex physiological system, and requires multiple cell types, which will necessitate a modular system with flexible control over physical properties and display of appropriate biological signals.

Figure 2:
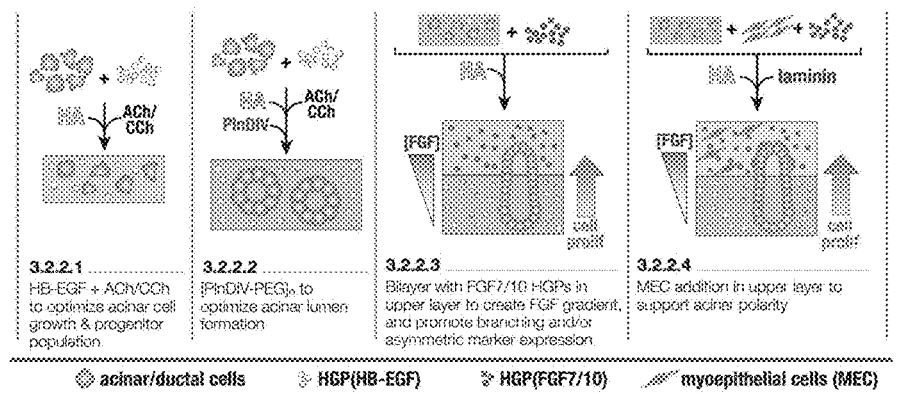
Figure 3:
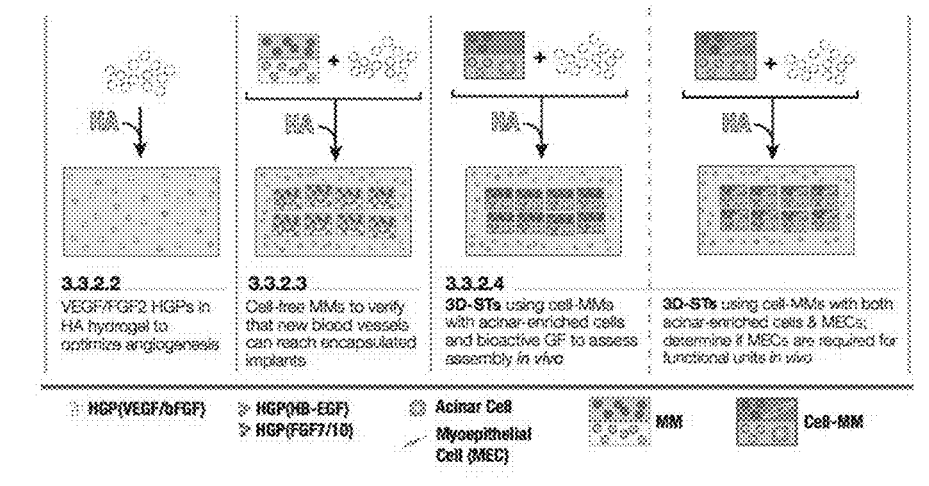

FIGS. 1 and 2 illustrate the steps involved for forming an implantable module hydrogel to aid in salivary gland restoration. An alternative embodiment is illustrated in FIG. 3.

Although the model described above may be specific for autologous transplantation, if may be combined with tissue typing and be useful for allografting as well. One concern with this approach would be the rejection of the implant.

In certain embodiments, the hydrogel networks of the present disclosure may be used to treat a subject suffering from xerostomia. In certain embodiments, the hydrogel networks of the present disclosure may be used to aid in salivary gland restoration.

In certain embodiments, the present disclosure provides a method of forming a hydrogel network comprising: providing a hyaluronic acid macromer; providing a multiblock copolymer, and crosslinking the hyaluronic acid macromer with the multiblock copolymer to form the hydrogel network. In certain embodiments, the multiblock copolymer comprises a multiblock copolymer of PlnDIV peptide alternating with PEG. In certain embodiments, the multiblock copolymer comprises a multiblock copolymer of poly (acrylic acid) (PAA) alternating with a hydrophobic peptide of sequence of $(VPGVG)_2$. In certain embodiments, the method may further comprise providing hyaluronic acid hydrogel particles. In certain embodiments, the hyaluronic acid hydrogel particles may comprise a growth factor and be capable of controlled release and delivery of growth factors.

In certain embodiments, the present disclosure provides a method of constructing a biomimetic matrix comprising: providing a hyaluronic acid hydrogel network, providing microscale densely crosslinked hyaluronic acid hydrogel particles, providing cells, co-encapsulating the hyaluronic acid hydrogel particles and the cells within the hyaluronic acid hydrogel network to form cell-laden microgel modules. In certain embodiments, the method may further comprise gelling multiple cell-laden microgel modules into a secondary hyaluronic acid network to yield macroscopic 3D-ST.

In certain embodiments, the present disclosure provides a kit comprising a hyaluronic acid macromer and a multiblock copolymer.

To facilitate a better understanding of the present disclosure, the following examples of certain aspects of some embodiments are given. In no way should the following examples be read to limit, or define, the entire scope of the disclosure.

EXAMPLES

Example 1

Materials and Methods: An IRB approved tissue collection protocol was established and salivary tissue was obtained from patients undergoing surgery. Tissue specimens were dissociated to obtain cultures of human salivary acinar progenitor cells. In order to mimic the native glandular tissue, a biocompatible and biodegradable hyaluronic acid (HA) based HYSTEM™ hydrogel system (Glycosan Biosystems, Salt Lake City, Utah) was utilized to encapsulate cells in 3D. Encapsulated salivary acinar progenitor cells rapidly formed 3D spheroid structures with lumen and retained typical salivary biomarkers. The spheroid structures demonstrated functionality by responding to stimulation by neurotransmitter agonists that activated their protein and fluid production pathways.

Results: In order to investigate the long-term survival and structure retention of salivary gland spheroids in vivo, these cell-seeded HA hydrogels were implanted in an animal model. Immunocompromised hooded athymic rats were used to avoid rejection of human salivary cells by the rat immune system. HA hydrogels containing salivary spheroids were implanted subcutaneously in the backflaps of nude rats. The implanted HA hydrogels maintained biocompatibility with the host and degraded significantly by four weeks. Encapsulated cells maintained viability for over three weeks and retained salivary biomarkers such as α-amylase, cytokeratins, and junctional proteins in vivo. Encapsulated salivary cells also maintained their spherical luminal structure throughout this time. In order to surgically simulate acinar cell loss, a parotid gland resection model was developed in which ¾ of the left parotid gland of a nude rat is resected. The right parotid is left intact so that there is minimal detriment to the animal from the reduction in saliva and also acts as a control. Acellular HA hydrogels in the parotid bed showed vascularization by the host at the one-week time point. Cell-seeded hydrogels, in the ¾ resection model, maintained viability of the encapsulated spheroids and expression of their phenotypic biomarkers in vivo. In an effort to increase angiogenesis into the implant, HA hydrogels were engineered to include VEGF loaded HA particles. Preliminary studies with acellular HA hydrogels containing VEGF loaded HA particles, implanted in the ¾ resected parotid bed, showed a robust increase in angiogenesis in one week. Future studies will involve long-term implantation of cell-seeded HA hydrogels with VEGF loaded particles in the parotid resection rat model, to assess the functionality of these engineered gels in vivo.

Conclusion: A hydrogel culture system capable of supporting 3D salivary spheroid structures in vivo was established. The hydrogel culture system reported here will aid the development of an artificial salivary gland that can be used to relieve symptoms of patients suffering from xerostomia.

Example 2

Figure 7:
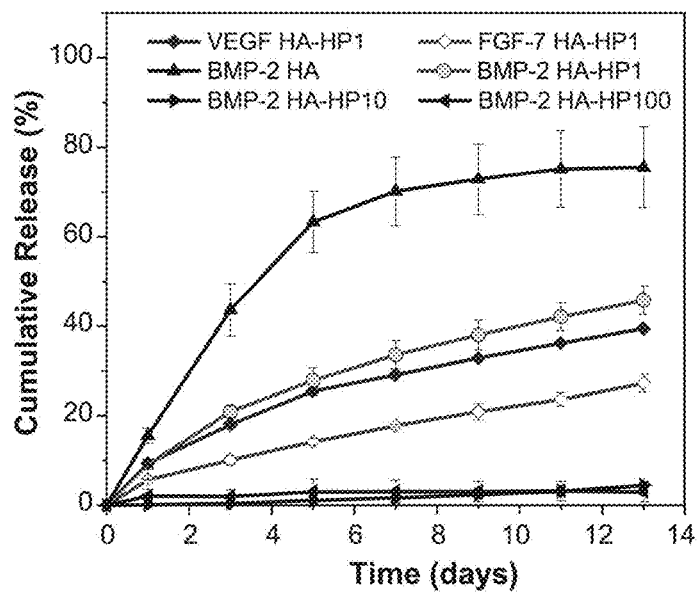

HA-based, doubly crosslinked networks (DXNs) have been developed that are hierarchically structured, mechanically robust and biologically active. In these systems, HGP spheres of micro- to nano-dimensions are embedded within porous HA hydrogel matrices (as shown in FIG. 4). HGPs are chemically functionalized to crosslink with both the HA hydrogel matrix, and with other HGPs, enabling tailored viscoelasticity, enzymatic stability and structural integrity, essential for tissue regeneration. These properties can be easily tuned by varying the size and number of HGPs, the crosslinking chemistry, and the density of the primary and the secondary networks. HGPs also deliver and release therapeutic GFs at targeted locations and controlled rates (as shown by FIG. 7) to elicit desired cellular behavior. Salivary gland-specific materials based on HA DXNs may employ dynamic biological and mechanical features to promote and control morphogenesis.

Separately, hybrid alternating copolymers that mimic the chemical, structural, and mechanical properties of natural ECM proteins have been created. Mimetic hybrid copolymers containing PEG alternating with the alanine-rich, lysine-containing peptide $(AKAAAKA)_2$ were synthesized and tagged with a fibronectin-derived RGD peptide. The resultant multiblock copolymers, when covalently crosslinked, have mechanical properties similar to natural elastin and are capable of supporting the attachment and proliferation of fibroblasts. Similar hybrid multiblock alternating copolymers of poly(acrylic acid) (PAA) and a hydrophobic $(VPGVG)_2$ $(_{VG}2)$ peptide from natural elastin self-assemble into stable, pH-responsive nanoparticles in aqueous solution. These soft, hybrid materials can incorporate specific epitopes to make them attractive materials for salivary gland tissue engineering.

HA plays critical roles in cell signaling, embryonic development and tissue morphogenesis, underscoring its potential as an instructive hydrogel matrix for salivary gland tissue engineering. HA DXNs may be constructed from modular building blocks at both the molecular and microscopic levels. The hydrogel network may be formed by crosslinking HA macromers with a multiblock copolymer of PlnDIV peptide alternating with PEG. These $[PlnDIV-PEG]_n$ copolymers may provide additional cellular cues in the HA matrix, amplified through multivalency to elicit coordinated and dynamic cell-matrix interactions. Michael-type addition reactions may be employed between sulfhydryl groups on the $[PlnDIV-PEG]_n$ copolymer and reactive double bonds on HA to form the secondary network. This reaction occurs rapidly at pH 7, resulting in a thioether bond with no toxic byproducts. Hydrogel stability can be tuned by varying the neighboring groups to the thioether. Within this matrix, HGPs may be co-encapsulated, and may release HBGFs sequentially in a controlled manner to induce cellular differentiation and tissue morphogenesis in situ. The modular nature of the building blocks allows for fine-tuning of the biological and biomechanical properties of the resulting matrix.

HA derivatives carrying unsaturated double bonds (HA-AC, as shown in FIG. 6) may be prepared by reacting adipic acid dihydrazide (ADH)-modified HA (routinely synthesized in the Jia Group with a degree of modification of 32-37%) with N-hydroxysuccinimide-activated 2-carboxyethyl acrylate oligomers $(NHS-[2CE]_nAC)$ in HEPES buffer at pH 7.2. Varying reaction stoichiometry will vary the % acrylate incorporation. The hydrolysis rate of the thiol-acrylate adduct may be adjusted by altering the number of ester repeats in $NHS-2-[CE]_nAC$. The product may be purified and characterized by standard means prior to use.

$[PlnDIV-PEG]_n$ multiblock crosslinkers may be synthesized via condensation polymerization using copper(I)-catalyzed alkyne-azide cycloaddition reaction (CuAAC). Azide-terminated, telechelic PEG with $M_n$ of 400, 1,450, 3,400 and 5,000 may be synthesized and purified. PlnDIV peptide may be tagged with the non-natural amino acid, propargyl glycine, to facilitate CuAAC coupling between peptide and $\alpha,\omega$-azido PEG. The functional group tolerance of CuAAC and the modular nature of the synthesis permit ready adjustment of the composition of the multiblock. To render the multiblock copolymers crosslinkable towards HA-AC, a cysteine residue may be added to the basic peptide sequence. The peptide motifs may be X(PlnDIV)XGGC, where PlnDIV will have a sequence of TWSKVGGHLRPGIVQSG, X is propargyl glycine, G is a gly spacer and C is a cys tag. Peptides may be prepared by solid phase peptide synthesis and purified. The $[PlnDIV-PEG]_n$ products may be purified and characterized by standard means. Filtration through Cuprisorb resin and dialysis against thiourea, imidazole, NaCl, and pure water solutions may yield polymers that are non-toxic to cells.

Salivary gland morphogenesis and angiogenesis require precise coordination among multiple GFs, including HB-EGF, FGF2, FGF7, FGF10 and VEGF. The proposed bioactive HA matrices will contain local GF stores capable of controlled delivery. Covalently immobilized PlnDI(HS) or heparin (HP) on HGPs may be used for the non-covalent association of the HBGFs, allowing HBGFs to form latent complexes through their specific binding. Such strategies offer the potential for sustained release over timescales relevant to controlling the initial cellular assembly in vitro and subsequent angiogenesis of the neotissue in vivo. It has been shown that HGPs, covalently functionalized with PlnDI(HS), can sequester BMP-2, modulate its release, and potentiate its biological functions, both in vitro and in vivo. Similar sustained release of BMP-2 may be achieved using HGPs with covalently integrated HP (see FIG. 7). HGPs with 0.55 µg HP/mg HGPs (HA-HP1), may release both VEGF and FGF-7 in a controlled manner, with faster VEGF release than FGF7. This is not surprising given the higher dissociation constant $(K_d)$ for VEGF/HP (165 nM) complex than for FGF7/HP (30-49 nM).

Covalently immobilized PlnDI(HS) or HP may be used for non-covalent GF association. Sequential GF release may be achieved by tailoring GF affinity for HGPs via the variation of HS/HP content in the particles. When HS/HP content is high, GF release is slow, as locally dissociated proteins are rapidly recaptured by unoccupied HS/HP sites before they can diffuse into the surrounding medium. When HS/HP content is low, GF is rapidly released through diffusion. It has been demonstrated that controlled BMP-2 release by HA/HP hybrid particles, along with the innate bioactivity of HA, induced robust and consistent chondrogenic differentiation of mesenchymal stem cells. The relative amount of HP incorporated in HGPs may be easily tuned by varying the HA/HP ratio in feed during particle synthesis, but modulation of PlnDI(HS) content may require multiple steps. Recombinant PlnDI(HS) with a C-terminal cysteine (5 residues into domain II) may be generated in the lab, and can be coupled easily to acrylated HGPs via the same Michael addition described above. HGPs with varying particle diameter and average interior pore size will be synthesized by inverse emulsion polymerization, following our previously reported procedures with minor revisions. The amount of HP/HS conjugated to HGPs may be varied and the % incorporation may be analyzed collectively by alcian blue staining, toluidine blue assay and chemical analysis.

The simplicity of particle synthesis, and the defined biological activities of the constituent building blocks, render the HS/HP-decorated, HGP system an attractive candidate for the sustained release of the proposed GFs. GF binding and release for all GFs may be quantified using immunochemical (ELISA) and radiolabelling assays. The content of the HGPs may be systematically varied to enable the sequential release of HBGFs. HGPs with a higher amount of PlnDI(HS) may be needed for the delayed release of VEGF than for the release of FGFs. Within the FGF family, the affinity of different variants for HS/HP may be similar. Thus, careful titration of HS/HP content may be critical to attain a defined gradient for each FGF. The combined HA gel, embedded HGPs and conjugated GFs may instruct salivary cell organization and tissue integration.

Successful engineering of functional salivary gland tissues may require robust, yet soft and pliable matrices that foster cell growth and differentiation, facilitate cell assembly and induce branching morphogenesis and tissue integration. From modular building blocks, 3D instructive matrices may be constructed by mixing HA-AC and [PlnDIV-PEG]$_n$ with GF-containing HGPs at varying proportions. Hydrogel crosslinking kinetics may be monitored via bulk solution rheology to determine gelation time and moduli of the stably crosslinked gels. Gels may be characterized via standard compression tests to probe stress-strain behaviors, stiffness and toughness. GF diffusion within hydrogel networks relates to hydrogel microstructure, and may be probed using fluorescently labeled GFs in fluorescence recovery after photobleaching (FRAP) self-diffusion studies. Bulk release studies will measure GF release rates from gels. Cytocompatibility of the composite, hybrid gels may be analyzed by mixing cells with the modular gel components for in situ gelation, and assaying for viability via live/dead staining.

Figure 8:
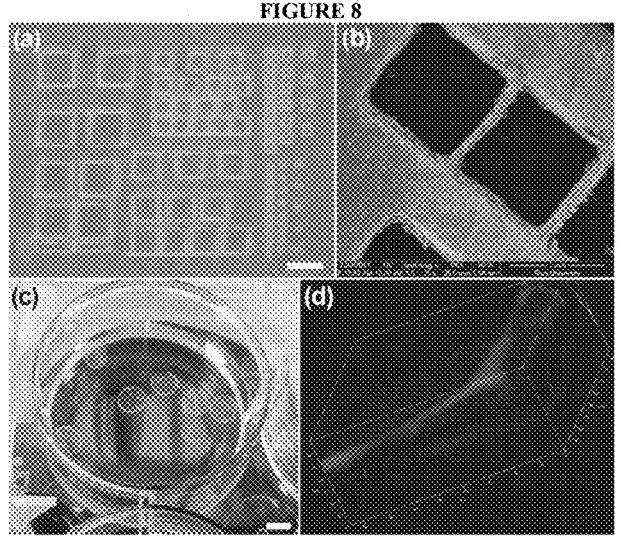

Cells may be encapsulated within miniature hydrogel modules for later reassembly into larger, more complex structures. As shown in FIG. 8, thin silicone (PDMS) slabs may be cured and a laser cutter may be used to create templates with scalable x,y features ranging from 200 μm to several millimeters, and similar z thickness. These PDMS molds are easily sterilized and reusable, with no changes in template dimensions. HA hydrogels may be gelled within these molds, and easily removed after gelation (See FIG. 8C). Adjacent bilayers with distinct cellular and biological components may be gelled (See FIG. 8D). PDMS molds may be adhered to glass substrates, and individual wells may be partially filled with a mixture of HA-AC, [PlnDIV-PEG]$_n$ and cells. As the HA precursors crosslink, cells may be encapsulated within the hydrogel network over 15-30 min. The molecular weight of the HA precursors may be tuned to allow for rapid diffusion, efficient crosslinking, and optimal mechanical properties.

Figure 9:
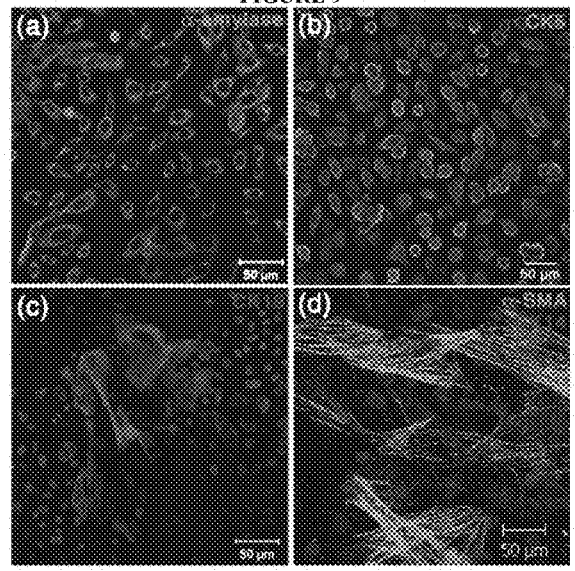

If disulfides interfere with the CuAAC reaction, acetamidomethyl group-protected cysteine may be used instead and the reactive thiol may be revealed by iodine oxidation upon completion of the condensation polymerization. The proposed multiblock crosslinker may contain a cysteine thiol on every peptide repeat. The close proximity of the thiol groups may cause the multiblock copolymers to form aggregates, stabilized by disulfide bonds. The cysteine thiol in the multiblock copolymer may be diluted by CuAAC of $N_3$-PEG-$N_3$ with a mixture of cysteine-containing and cysteine-lacking peptide monomers. The modular nature of the design, coupled with the chemical nature of the synthesis, may permit facile adjustment of mechanical, morphological, and biological properties of the resulting matrices. PlnIV peptide may be conjugated to HA-AC to provide essential cues to cells entrapped in the Cell-MMs. If PlnIV peptide alone is not sufficient to elicit cell attachment and assembly, laminin-derived peptide with a sequence of IKVAV and YIGSR or fibronectin-derived RGD can be integrated into hydrogels to reinforce the biological activity of PlnIV peptide. FIG. 9 demonstrates HA bilayers with dimensions down to 200 μm. Standard microfabrication methods may be used to produce bilayers with smaller dimension.

The salivary gland is a complex glandular tissue built upon the core synthetic and secretory function of polarized salivary acinar cells, the directional pipeline established by the assembled ductal cells, and the stimulated MECs. Regulated saliva transport into the oral cavity absolutely depends upon glandular integration with vascular and autonomic nervous tissue. The biological principles by which this assembly occurs during salivary gland organogenesis are increasingly well understood. This disclosure re-establishes these principles to the best of sum current knowledge in a modular tissue engineering approach to build a neotissue 3D-ST ready for pre-clinical surgical implantation.

Purified primary human salivary $CK5^+$ progenitor cell-enriched populations (as shown in FIGS. 9A and 9B) with long term (>100 day) growth potential that appears to be limited only by time and space when cultured in 3D HA hydrogels were developed. From these, human ductal and MECs with appropriate morphology and marker expression were obtained and cultured. (See FIGS. 9C and 9D.) Salivary acinar cells in 3D HA hydrogels such that they form stable tight junctions by multiple criteria were reassembled. (See FIG. 10) Consistent lumen formation in acinar-like cells grown in 3-D was established. The synthesis and secretion of salivary amylase by salivary acinar cells in 2D, 2.5D, and 3D was demonstrated. Responses of salivary cells to both muscarinic and β-adrenergic stimulation (See FIG. 16) were demonstrated. Conditions for transfections of cultured acinar-enriched cells with red fluorescent protein (RFP) were developed. Conditions for reproducible induction of angiogenesis using FGF-2 and VEGF were established.

Strategies to build an artificial salivary gland suitable for implantation may incorporate the following 7 features: 1) instill cellular growth potential without overgrowth; 2) trigger and retain the differentiated, properly assembled branched state involving multiple cell types; 3) build and retain tight junctions among polarized acini; 4) create and retain proper luminal structures for accumulation and transport of salivary components (fluid and protein); 5) support long term synthesis and regulated, directional secretion of salivary components; 6) establish and retain proper assembly of ECM components, cell and tissue barriers; and 7) recruit vascular and nervous tissue to maintain the gland and ensure tissue integration.

Figure 10:
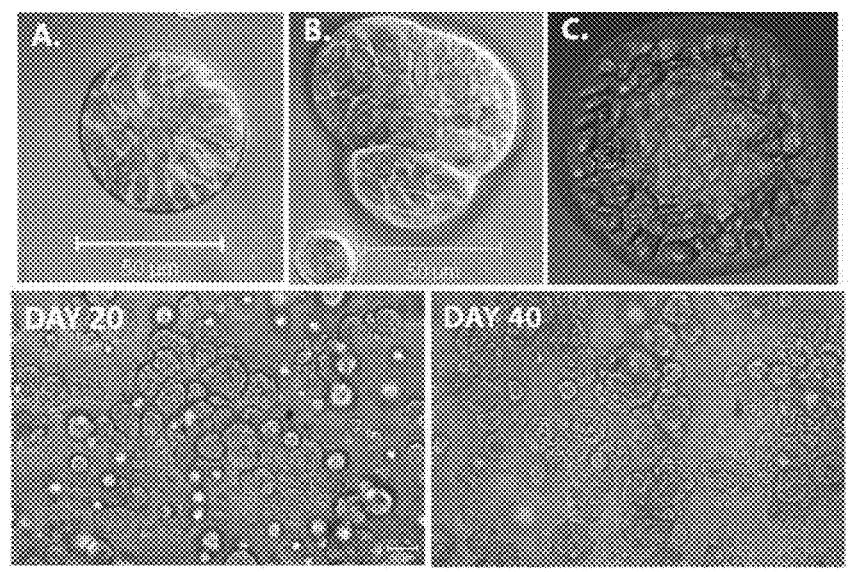
FIG. 10 is a picture that illustrates human acinar cells in 3D culture in HA hydrogels. (a-b) Stained for β-catenin (green), showing merging structures in (b); (c) reconstructed confocal microscopy images featuring nuclei (blue), SYTO13 (green), and propidium iodide (red). Images demonstrate extended cultures with large acinar structures at day 20 and 40.
Figure 11:
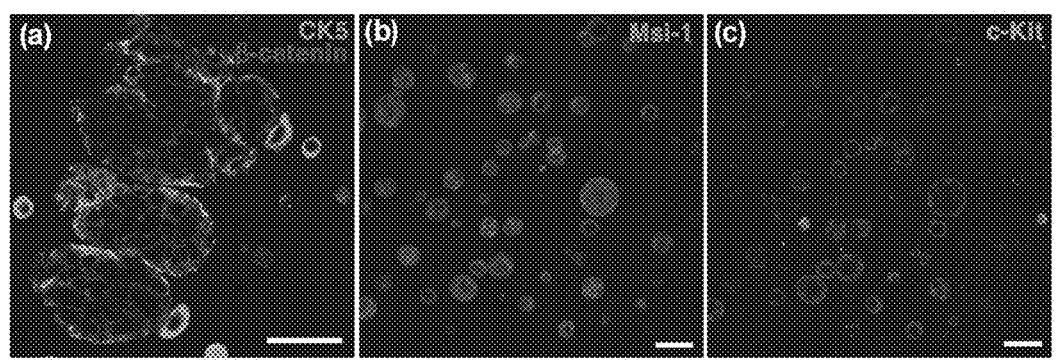
FIG. 11 is a picture that depicts the expression of progenitor markers in 3D HA cultures. (a) CK5 expression throughout mature spheroids, co-stained for β-catenin at cell-cell junctions; (b,c) Msi-1 expressed throughout spheroid cell aggregates, with c-Kit visible at peripheries.
Figure 12:
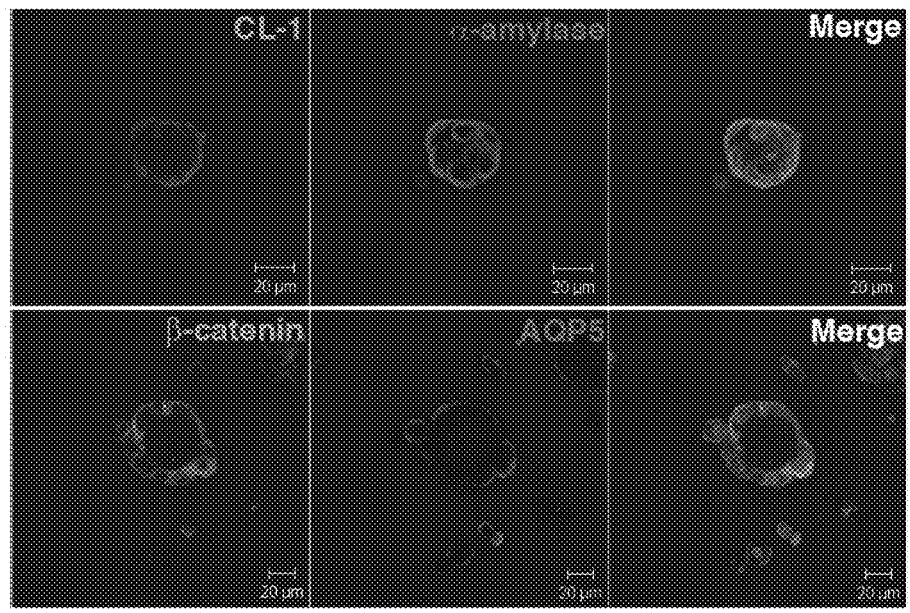
FIG. 12 is a picture depicting organized spheroids on PlnDIV-HA gels. at early timepoints. Note lumen formation in lower right image.

In 2D culture, salivary acinar cells can senesce, a property that limits efforts to functionally reconstitute a full gland. Such growth limitations are not found in 3D HA hydrogels (as shown in FIG. 11), in which cells continue to grow over three months and appear to be limited only by space constraints in the hydrogel. Recent reports indicate that long-term survival of the progenitor cell population that continuously reconstitutes the salivary gland through the life of the organism requires multiple stimuli, including signals from parasympathetic innervations. In particular, cytokeratin 5 (CK5) progenitor cells positive for both muscarinic receptor M1 and epidermal growth factor receptor (EGFR) are maintained through signaling by acetylcholine (ACh) or its stable analog carbamylcholine (CCh), and HB-EGF. It has been observed that, in 2D, the isolated primary human acinar cells are >99% $CK5^+$ (as shown in FIG. 9B) with moderate c-Kit expression. As these cells form assembled acini-like structures in the 3D HA hydrogels (as shown in FIG. 10), CK5 expression is retained, along with expression of Musashi-1 (Msi-1), and peripheral c-Kit. Msi-1 and c-Kit are widely described as markers for cells with progenitor and/or proliferative potential.

HGPs pre-loaded with HB-EGF and isolated acinar-enriched cells may be embedded within HA microgels. Culturing these MMs with varying CCh levels and varying HB-EGF release rates may allow for the determination of if a stable $CK5^+$ population is maintained or enhanced in the acinar-enriched and/or ductal-enriched cultures during long term culture. The effects of varying these factors may be assessed by measuring cell proliferation (via PicoGreen) and staining for CK5, c-Kit, Msi-1, Ki67 (proliferation), and phenotypic markers Fgfr2b, CK19, and α-amylase. Cell response to CCh and HB-EGF stimulation may be quantified, either through in situ immunostaining and imaging of cell-MMs, or through cell release from the HA gels, followed by flow cytometry. The necessity of co-culture with MECs and/or ductal cells to maintain acinar cell growth and differentiation may also be assessed. Best practices for ensuring growth of salivary cells in Cell-MMs and for maintenance of the progenitor cell population needed to resupply 3D-STs post-implantation may be established.

Figure 14:
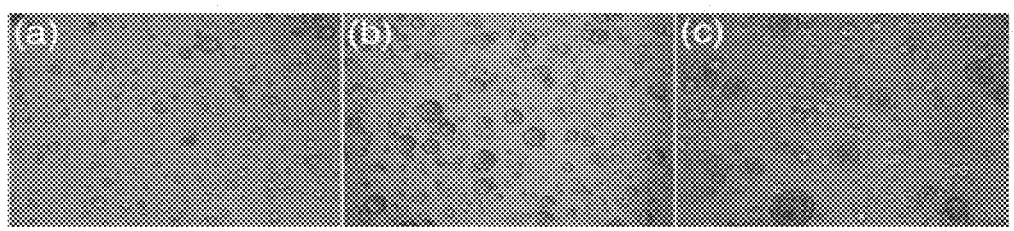
FIG. 14 is a picture depicting organized spheroids. FGF7 treatment increases spheroid size in 3D HA hydrogels. (a) Untreated cells at 20 d culture. (b,c) Spheroids treated with 25 ng/mL FGF7 daily for (b) 10 d and (c) 12 d.
Figure 15:
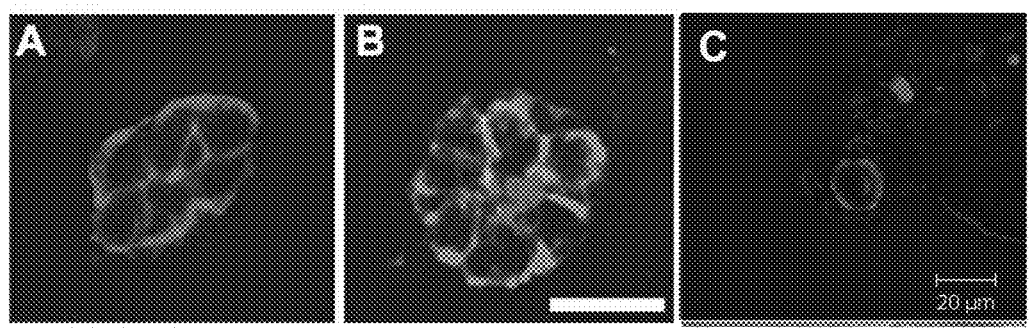
FIG. 15 is a picture depicting ZO-1 staining. ZO-1 staining (red) in breast (a-b, from, demonstrating (a) "inside-out" acini polarity, and (b) correct stable polarity induced by MEC contact; (c) 3D acinar spheroid culture on our HA hydrogels, showing a mixture of peripheral (i.e. inverted) ZO-1 expression, and correct luminal expression of Muc1.

Tight junction formation may be a hallmark of epithelial cell-cell interaction, and is well-characterized in salivary gland morphogenesis. Primary acinar-like cultures in HA quickly organize (~6 days) to form stable spheroids with defined lumen, apoptotic interior cells, and a gradually expanding diameter (as shown in FIG. 14). Pln in basement membranes is key to acini formation in developing glands, and enhanced spheroid formation through the covalent incorporation of PlnDIV peptide into the HA matrix has been observed. It has been shown that epithelial cells preferentially interact with this peptide, and that salivary acinar cells organize in PlnDIV-modified HA matrices leading to (a) enhanced lumen formation and (b) expression of tight and/or adherens junction markers (E-cadherin, β-catenin, claudin-1, ZO-1) (as shown in FIG. 15).

Figure 13:
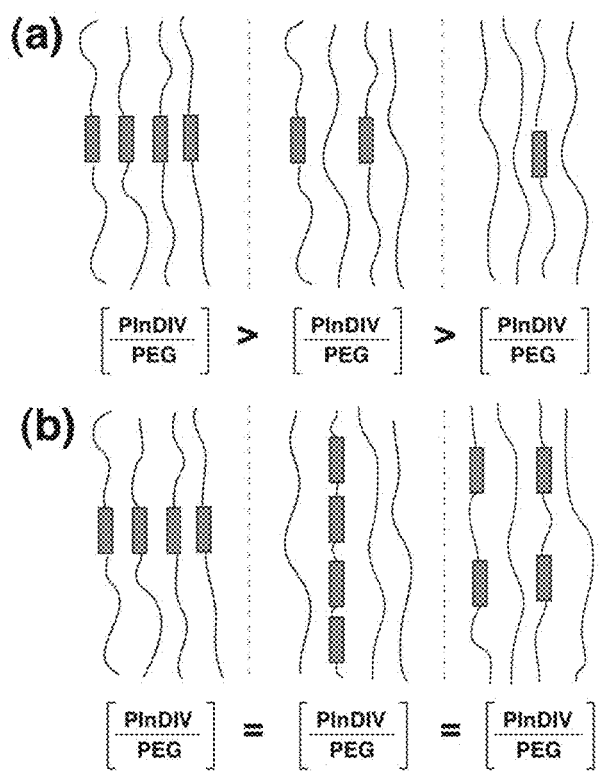
FIG. 13 is a drawing that illustrates method for varying PlnDIV global and local levels.

PlnDIV-functional copolymers may be diluted with plain PEG, to maintain a constant gel crosslink density. PlnDIV concentration may be varied in two ways (as shown in FIG. 13): (a) varying the overall PlnDIV:PEG molar ratio within each gel, and (b) holding PlnDIV:PEG constant, but varying the number of PlnDIV peptides per copolymer chain. The latter experiment (b) may identify the impact on cell behavior of high local (i.e. clustered) PlnDIV peptides, which replicates their presentation in the 21 Ig repeats of Pln DIV. This range of experiments is made possible by the use of Cell-MM microgels, which are easily replicated in high numbers for multiple experiments with high throughput, and easily imaged. Cell response can be quantified by immunostaining of cell-MMs for tight and/or adherens junction markers (E-cadherin, β-catenin, claudin-1, ZO-1) and HA receptors (RHAMM, CD44), measurement of acinus size/number of time, and qualitative observations of acinus morphology.

Functional neotissue glands must advance beyond spherical lumen to initiate directional delivery of secretory products, and recreate the differentiated roles of fluid producing acinar and fluid resorbing ductal cells. Recent work identified the specific roles of FGF7 and FGF10 in inducing ductal elongation and branching, respectively. These roles are tied to the cells' perceived gradients of each GF from a point source, defined by diffusion through ECM and controlled by their binding to HS (in Pln and other proteoglycans). Similar responses to FGF7 from assembled acinar-like cells in the 3D HA systems have been seen, indicating that they have functional Fgfr2b. When delivered through media, FGF7 may induce overall larger spheroids (as expected, when FGF7 is not delivered from a directional point source). This response suggests that the acinar-enriched cell populations in the hydrogels retain proliferative potential and have not reached a post-proliferative stage of terminal differentiation. HGPs are an optimal mechanism for directional controlled delivery of FGF7 and FGF10.

A second layer of HA hydrogel, containing HGPs loaded with FGF7 and/or FGF10 may be added. In this two-step modular process, acinar cells may be encapsulated in an HA "bottom layer" with the proper levels of CCh, HB-EGF HGPs, and PlnDIV. After gelation, a second thin layer of HA with FGF7/10-HGPs may be gelled above. Providing a directional mitogen gradient for the salivary cells may promote the formation of more complex, asymmetric structures, which may more accurately replicate native tissue. FGF7/10 levels may be varied by total amount, and by release rate. These two-layer systems may be assessed for morphological changes (e.g. aspect ratio, bud ratio), and differential immunostaining at the distal edges vs. the proximal origin, and may be compared to control systems with FGF7/10 HGPs co-mixed within a single layer.

Cues from ECM and neighboring cells may provide essential information to initiate and maintain stable long term differentiation of gland structures arising through processes of branching morphogenesis. In the breast, inside-out acini reverse to correct stable polarity in the presence of MECs or a bioactive laminin-based peptide mimetic. Developmental studies showed similar invasion of epithelial precursors into a neighboring mesenchymal space, following GF cues from mesenchyme. The expanded 3D cultures already maintain many features expected of functional glands including stable tight junctions, enzyme production, and ion and water channels, an exception being their lack of final apical distribution of Muc1, a late polarization marker (See FIG. 16).

Cultured MECs may be seeded with FGF7/10 HGPs in the "upper" layer of an HA bilayer. By creating a secondary HA layer above our acinar/ductal system, this may allow for sequential timing of acinar/ductal pre-organization in the bottom layer, prior to advancing into the upper MEC compartment. Laminin and/or PlnDIV peptide motifs may be covalently bound in the upper layer as needed, to promote MEC/ECM adhesion. Admixing of the two layers may be used for comparison. Each cell type can be fluorescently labeled to identify their movement, morphology, and association throughout the gels. Cell association among the seeded populations may be assessed, as well as the redistribution of Muc1, to correct luminal orientation.

FIG. 16 demonstrates the expression of β1 and β2 adrenergic receptors, and the M3 muscarinic receptor in spheroids assembled in HA hydrogel cultures. While staining was moderate and diffuse in 2D cultures, its intensity and localization within cell aggregates in HA hydrogels was robust and paralleled the staining observed in native tissue. Treatment of assembled spheroids in HA with norepinephrine induced granule formation and robust α-amylase staining at the cell periphery and within the secretory route, indicative of a secretory exocytic response, while ACh treatment induced $Ca^{2+}$ spikes (measured by Fluo-4) within the cells, indicative of a $Ca^{2+}$-based second messenger response. These responses were observed in assembled spheroids in HA hydrogels, but not in 2D cultures or isolated cells on HA, emphasizing the importance of spheroid assembly and tight junctions.

PEG-PlnDIV synthesis is based on well-developed chemistry. If problems arise, acrylated or thiolated PlnDIV may be synthesized for direct pendant incorporation into the HA network. For FGF7 experiments, it is known that specific interactions occur between FGF7 and the N-terminal segment of Pln domain III. PlnDIII core protein fragments may be incorporated into HGP particles as a secondary FGF7 source if warranted. FGF7/10 HGPs may affect MECs in the upper layer of cell-MMs, as is known in other glandular tissues. FGF7/10 levels may be modified as needed, or control trials may be conducted with empty HGP to troubleshoot the upper layer if MECs are adversely affected.

Restoration of glandular tissues has lagged behind recent progress in bone, cartilage and bladder engineering, in part due to the increased cellular complexity of the tissue. In vivo studies may implant engineered human salivary gland prototypes of progressive complexity, and test their function at each step. These studies may yield an experimental framework for assessing function in vivo for salivary tissues. Optimized MMs and 3D-STs (See FIGS. 1 and 2) may be implanted in a rat model and monitored over time. Outcome measures may assess the functions that must be reestablished by the implant and the known structural features of native salivary tissue. Immunocompetent Sprague-Dawley rats may be used for cell-free MMs, while the hooded T cell deficient athymic nude rat may be the model for cell-MMs, because it is of sufficient size to host surgical implants and its immunocompromised status allows use human cell use without rejection.

HA gels (acellular, GF seeded, and acinar cell seeded) have successfully been implanted subcutaneously in the back of nude rats and in the ¾ resected parotid gland model that we developed with minimal detriment to the host. None of these constructs induced inflammation, but unvascularized gels were degraded significantly after 4 wks in the back (See FIG. 17B). Encapsulated CK5+ cells remained viable for >3 wks and a majority of implanted spheroids continued to produce amylase, express cytokeratins, and maintain luminal structure (See FIGS. 17C and 17D). To assess the ability of HGPs to trigger angiogenesis into the HA hydrogels, gels containing VEGF loaded HGPs were implanted in the ¾ resected parotid bed. In 1 wk, implants in the parotid bed showed a robust increase in blood vessel formation and infiltration into the gel implant (See FIG. 17F). Cell-MM and 3D-ST studies thus may include cells fully embedded in various test constructs of hydrogel. Based on the initial animal studies, viability or biocompatibility problems are not expected with HA, Pln-HA constructs, or human acinar cells in the nude rat system or cell free modified hydrogels in immunocompetent rats.

Proof-of-principle studies in rats implanted with 3D-ST may be conducted. These studies may evaluate implant viability, integration into the surrounding tissue, recruitment of vascular support (via our controlled GF release methods), and restoration of salivary function. The strategy is to surgically simulate acinar cell loss through controlled parotid resection, with subsequent replacement during the same surgery with engineered 3D-STs and outcomes assessment (structure, function, tissue integration). At UD, an IACUC-approved protocol is in place for these studies (details in Vertebrate Animals). A surgical model was developed in which ¾ of the left parotid gland of 5 male rats per group (consistent with similar pilot studies is resected, leaving the right side intact as a control. Resected salivary gland tissue does not regenerate in humans, and is not expected to regenerate in other mammals. However, the remaining salivary duct structure and function may be preserved, as has been shown for ducts blocked by stones. Sterile dissection of the rat requires a small incision with exposure of the rat parotid and preservation of neural tissue. 3D-STs are embedded in the left rat parotid gland, a procedure to date with minimal detriment to the animal subjects.

Prior to RT, patients can undergo ultrasound guided fine needle aspiration to visualize normal parotid parenchyma free of tumor. Under the IRB-approved protocol, tissues may be secured from consenting patients, and these tissues may be immediately processed in the laboratory to release, sort, and culture the $CK5^+$ progenitor cell populations that contain the various acinar, ductal, and MEC populations. A bank of these cells from multiple patients, taken from multiple gland sites, may be maintained and these cells may be used to generate all preliminary data.

Implanted neotissues of any significant size require a blood supply for their long-term survival in vivo. Neovessels must be able to reach any encapsulated cell-MMs. Increases in angiogenesis into the HA hydrogels containing VEGF-loaded HGPs (200 ng/mL) over control hydrogels implanted in the parotid bed have been demonstrated (See FIG. 17F). The HGPs may be tuned to recruit vascular supply in vivo, and quantifying the resultant capillary structure. The volume of implanted hydrogel may also be varied, to insure that neovessels can reach any cell-MM structures within.

HGPs may be pre-loaded with both VEGF and FGF2 to induce capillary ingrowth from surrounding tissue, a combination found to be synergistic in stimulating angiogenesis. A pre-set number of HGPs, at three GF concentrations (0, 10, 100 ng/mL), may be gelled within HA networks at two volumes (150 and 300 μl) to form an HA-HGP structure. HA-HGP may be implanted in 4 month old immune intact Sprague-Dawley rats after ¾ left parotid resection. After 1 and 4 wks (earlier in case of adverse event), implants may be harvested, processed, immunostained, and assessed for angiogenesis in the HA-HGPs by the presence of vascular elements (CD31/PECAM+), and their length, branches, and nodes. Histologic sections may be stained for inflammation or immune cell response (T cell, neutrophil, macrophage). Any combination causing adverse host immune responses may be discarded. HA-HGPs with the best host response profiles (quantified vessel length, branching) may be used for cell-seeded implant studies in the parotid in nude rats. The distance of accessible vascularization may be used to set the final volume for later 3D-STs.

A series of comparative studies may incorporate the bilayered MM structures, which employed HGPs loaded with HB-EGF in one layer, and FGF7/10 in the other. MMs may be encapsulated within HA to form larger 3D-ST modular objects. Cell-free 3D-STs may be implanted in the left parotid bed of 4 month old ¾ resected Sprague-Dawley rats and allowed to mature for 4 weeks if there are no adverse effects. After sacrifice, implants may be scored for vascularization and immune response.

Optimized angiogenic HGPs and MECs may be systematically introduced within cell-MMs to determine if these supporting mechanisms are necessary and/or sufficient to promote acinar retention, organization, and phenotype expression in vivo. Cell-MMs may employ RFP-transfected acinar progenitor-enriched cells for monitoring over time in implanted rats in vivo via IVIS imaging (Caliper). Fluorescence has previously been detected from as few as 1000 cells, with strong signal from >5000 cells if no hair was present, thus nude rats are ideal. Fluorescence intensity may correlate to growth of implanted RFP-labeled cells in vivo.

As shown in the Vertebrate Animals table, the in vivo experiments may be divided into four implantation groups, varying two parameters: (a) 3D-STs with/without angiogenic HGPs and (b) 3D-STs with/without MEC support cells. All groups may be implanted in the left parotid bed of ¾ resected nude rats, monitored at 1, 4, 7, or 10 wks by in vivo IVIS imaging. At experiments end, implants may be retrieved and quantified for vascularization as before. RFP$^+$ cell retention and co-localization with specific biomarkers may be quantified by IHC: (1) progenitor markers (CK5, c-Kit, Msi-1); (2) proliferation marker Ki67; (3) ratios and location of α-amylase/K14/K19$^+$ cells (acinar/MEC/ductal cell differentiation); (4) FGFR2b. Morphologic analysis may assess if the acinar-cell seeded Cell-MM triggers and retains: 1) differentiated and properly assembled acini-like structures; 2) tight junctions among polarized acini (E-cadherin, β-catenin, claudin-1, ZO-1 staining); 3) proper luminal structures for accumulation/transport of salivary components (aquaporin); 4) assembly of ECM components, cell and tissue barriers; 5) host salivary cells; 6) ductal cell differentiation in situ. Any connections between the implanted structures and the innate salivary and vascular supply may be highlighted and quantified. All structures may be compared to intact salivary tissues in the same animal. Supporting work may utilize Western blot and RT-PCR to qualitatively and quantitatively measure acinar cell phenotype including basement membrane protein expression and secretion, tight junction proteins, water channel protein aquaporin-5, stress fibers, activated focal adhesion kinase, and α-amylase as in our previous published work. TUNEL and/or caspase staining may assess apoptosis. Signs of necrosis, loss of cell viability, or host cell infiltrate that may occur even in the absence of T cells may be looked for. It is hypothesized that Cell-MMs, implanted without 3D-ST angio support, may not fare as well as the full 3D-ST assemblies. The survival of 3D-STs in the salivary bed may be assessed. It may be determined whether complex cell mixtures or acinar enriched cell populations alone are needed to form neotissues. Also, the host response for optimal biointegration may be tuned. It may also be possible to determine if CK5+ populations expressing proliferative/progenitor markers can survive long term to provide the full resource for permanent in situ restoration of gland function (vs a need to resupply multiple more differentiated cell types), and potentially resolve unanswered questions in the current literature.

After evaluating 3D-ST function on the cellular level in, full in vivo function may be assessed through a series of physiological assessments. Cell-MMs within 3D-STs may be varied across four groups (0, 10, 50, or 250 Cell-MMs per 3D-ST) to determine the minimum number needed to restore salivary function. Each group may be implanted in ¾ resection surgeries in nude rats. At 1 and 4 wks after implantation, rats from each group may be anesthetized and injected with pilocarpine to induce salivation. Saliva may be obtained from the oral cavity using a micropipette and assessed using the following assays: (1) BCA assay (total salivary protein concentrations); (2) Western blot with human-specific antibodies against α-amylase, IgA, mucins, albumin, proline-rich, histatin-rich and tyrosine-rich proteins; (3) viscosity, pH and electrolytes; (4) quantification of functional amylase production by chromogenic assay Animals will be euthanized and implants will be analyzed histologically for tissue response, integrity, stability and biointegration of the implanted 3D-STs.

All quantitative data from outcome measures may be analyzed statistically via calculation of means, standard deviations, and standard errors. To determine significance, Student's two-tailed t-tests or Analysis of Variance (ANOVA) may be used. Significance may be defined as a confidence interval greater than 95% (p<0.05).

A successful, functional 3D-ST prototype may have greater protein, electrolyte, and water production after 4 wks implantation, with lower viscosity and higher pH. 3D-STs may show long term stability, biointegration, and no overgrowth. Cell differentiation should be maintained, and neither necrosis nor fibrosis should occur. Acellular 3D-STs supplied with GFs may stimulate remaining endogenous progenitor cells to repair the gland, a potential outcome that also would be a success.

FIG. 17 shows HA stability in vivo, human acinar cell retention, phenotypic lumen formation and amylase expression, and angiogenesis from the host. HA stability/degradation rate can be tuned through crosslink density if needed. Implanted human cells (MECs or acinar cells) can be identified after sacrifice using human-specific ribosomal RPL29 antibody, should RFP labeling fail. Because the resected parotid model does not create a condition identical to patients undergoing RT, future studies could use alternate facilities to irradiate the rodent salivary bed and follow acinar cell and tissue destruction. A neural stimulation to the implant is important. 3D-STs may be analyzed for innervation into the implant, by the presence and length of neuronal axons (via neuronal markers). If the implant fails to have any signs of innervation, HGPs can be modified to deliver NGF.

Example 3

This example illustrates salivary acinar-like cell assembly and functional neurotransmitter responses within 2.5D and 3D HA hydrogel systems both in vitro and in vivo. We reported the isolation of acinar-like cells from human salivary tissues, and their self-assembly into 3D acini-like structures when cultured on 2.5D hyaluronic acid (HA) hydrogels modified with ECM-derived bioactive peptide fragments. (Pradhan, S., C. Liu, C. Zhang, X. Jia, M. C. Farach-Carson, R. L. Witt. Lumen formation in 3D cultures of salivary acinar cells. Otolaryngology—Head and Neck Surgery, 2009). We recently employed a 3D HA-based culture system to organize salivary acinar-like cells into spherical structures.

The development of a tissue-engineered, implantable salivary gland will greatly benefit patients suffering from xerostomia. This example compares the ability of a 2.5D and a 3D hyaluronic acid (HA)-based culture system to support functional salivary units capable of producing fluid and phenotypic proteins. Parotid cells seeded on 2.5D, as well as those encapsulated in 3D HA hydrogels, self-assembled into acini-like structures and expressed functional neurotransmitter receptors. Structures in 3D hydrogels merged to form organized 50 μm spheroids that could be maintained in culture for over 100 days and merged to form structures over 500 μm in size. Treatment of acini-like structures with the β-adrenergic agonists norepinephrine or isoproterenol increased granule production and α-amylase staining in treated structures, demonstrating regain of protein secretion. Upon treatment with the M3 muscarinic agonist acetylcholine, acini-like structures activated the fluid production pathway by increasing intracellular calcium levels. The increase in intracellular calcium seen in structures in the 3D hydrogel culture system was more robust and prolonged than that in 2.5D. To compare the long-term survival and retention of acini-like structures in vivo, cell-seeded 2.5D and 3D hydrogels were implanted into an athymic rat model. Cells in 2.5D failed to maintain organized acini-like structures and dispersed in the surrounding tissue. Encapsulated cells in 3D retained their spheroid structure and structural integrity, along with the salivary biomarkers and maintained viability for over three weeks in vivo. This example identifies a novel hydrogel culture system capable of creating and maintaining functional 3D salivary spheroid structures for long periods in vitro that regain both fluid and protein secreting functions and are suitable for tissue restoration.

Cell Culture

Parotid gland tissue was collected from patients aged 40-55 years undergoing surgery under an IRB-approved protocol and consent from both Christiana Care Health Systems and University of Delaware. Homogeneous populations of proliferating acinar-like cells were obtained from tissue explant outgrowths and tissue dissociation procedures as previously described. (Pradhan, S., C. Liu, C. Zhang, X. Jia, M. C. Farach-Carson, R. L. Witt. Lumen formation in 3D cultures of salivary acinar cells. Otolaryngology—Head and Neck Surgery, 2009; Pradhan, S., C. Zhang, X. Jia, D. D. Carson, R. Witt, M. C. Farach-Carson. Perlecan domain IV peptide stimulates salivary gland cell assembly in vitro. Tissue engineering Part A 15, 3309, 2009.) Parotid gland tissue specimens were minced to a slurry that was suspended in serum-free Hepato-STIM medium (BD Biosciences Discovery Labware, Bedford, Mass.) and distributed in a six-well plate (BD Falcon™, Franklin Lakes, N.J.) and left untouched for 7 days, then supplemented with Hepato-STIM growth medium until cells migrated out of the tissue explants. Confluent cells were passaged with 0.05% (w/v) trypsin EDTA (Invitrogen). 0.5 mg/mL of trypsin soybean inhibitor (Sigma, St. Louis, Mo.) stopped the trypsin activity. Cells were plated at a dilution of 1:10. Cells in passage 3-4 were used for all experiments.

2D Hydrogel Preparation

HA was modified to contain methacrylate groups by reacting it with glycidyl methacrylate (GMA), as described previously (Jia, X. Q., J. A. Burdick, J. Kobler, R. J. Clifton, J. J. Rosowski, S. M. Zeitels, R. Langer. Synthesis and characterization of in situ cross-linkable hyaluronic acid-based hydrogels with potential application for vocal fold regeneration. Macromolecules 37, 3239, 2004.) This photocrosslinkable HA (HAGMA) was crosslinked into hydrogels in the presence of photoinitiator, 30% (w/v) 2,2-dimethoxy-2-phenylacetophenone (DMPA) in 1-vinyl-2-pyrrolidinone (NVP). Hydrogels were generated in cell culture inserts (Millipore, Billerica, Mass., diameter: 12 mm, pore size: 0.4 µm) and placed in 24-well plates (Corning, Lowell, Mass.). Polymerized gels were swollen in 1×PBS for 24 h. Salivary acinar-like cells were seeded on the hydrogels ($1\times10^5$ cells/200 µL hydrogel) and Hepato-STIM growth media was added both inside and outside the culture insert.

3D Hydrogel Preparation

An HA-based Hystem™ hydrogel system (Glycosan Biosystems, Salt Lake City, Utah) was utilized to encapsulate salivary cells in 3D. Cells ($1\times10^5$ cells/1500 µL hydrogel) were mixed with the HA-thiol component of the kit. Extralink [poly(ethylene glycol)-diacrylate] was added directly to this mixture, and mixed thoroughly before plating on 12 mm cell culture inserts (Millipore) placed in 24-well plates. Plates were placed in a 37° C. incubator for partial polymerization. After 15 min, a small amount of Hepato-STIM growth media was added to the outside chamber of the culture insert and the gel polymerized for 10 minutes. Upon complete polymerization, culture media was added over the hydrogel.

Analysis of Structure Growth $1\times10^5$ cells/hydrogel were seeded on the 2.5D and in the 3D HA hydrogels. Acini-like structures were counted from each quadrant of three such hydrogels, for every time point. Hydrogels were supplemented with 300 µL of media every 3 days for the first 12 days. After about 12 days in culture when the hydrogels are full of larger spheroid structures that metabolize rapidly, the media is exchanged every 3 days.

Cell Proliferation Measurements $1\times10^5$ cells/hydrogel were seeded in 3D and were maintained as mentioned above. Hydrogels were analyzed at Day 1, 6, 12, 21 and 26. On the day of analysis, media was removed and the hydrogels were washed with 1×PBS. 30 µL of 30 kU/mL hyaluronidase type VI-S (Sigma) was added to each gel and incubated at 37° C. for ~2 h. The cells were then pelleted and washed with 1×PBS. The cell pellet was resuspended in 200 uL of lysis buffer and cells were allowed to lyse for 30 min on ice. The solution was then centrifuged at 13,000 RPM for 20 min and the supernatant was used for further analysis. The Qubit™ dsDNA HS Assay Kit (Invitrogen) was used to measure dsDNA concentration using the Qubit® Fluorometer (Invitrogen).

Immunofluorescence

Primary antibodies were monoclonal claudin-1 (Zymed Laboratories, San Francisco, Calif.), polyclonal ZO-1 (Zymed Laboratories), monoclonal β-catenin (BD Transduction Laboratories), monoclonal E-cadherin (Abcam, Cambridge, Mass.), monoclonal Ki-67 (BD Pharmingen™) polyclonal M3 muscarinic receptor (Santa Cruz Biotechnology, Santa Cruz, Calif.), polyclonal β1 adrenergic receptor (Santa Cruz Biotechnology), polyclonal β2 adrenergic receptor (Abcam) and polyclonal α-amylase (Sigma, St. Louis, Mo.). Secondary antibodies Alexa 488 and Alexa 568 (Invitrogen, Carlsbad, Calif.) against mouse or rabbit IgG were used. Nuclei were stained with Draq5 (Biostatus, Leicestershire, United Kingdom).

Staining of tissue sections and 2D cultured cells was performed as previously described (Pradhan, S., C. Zhang, X. Jia, D. D. Carson, R. Witt, M. C. Farach-Carson. Perlecan domain IV peptide stimulates salivary gland cell assembly in vitro. Tissue engineering Part A 15, 3309, 2009). Briefly, tissue cryosections (8 µm) were fixed with cold 100% methanol, rehydrated with 1×PBS and blocked overnight in 3% (w/v) BSA in PBS. Sections were incubated with primary antibody at 37° C. for 45 min and washed in 1×PBS for 30 min. Secondary antibody incubation was for 40 min at 37° C. followed by 10 min treatment with Draq5. Tissue sections then were washed with 1×PBS for 30 min. Slides were mounted with Gel Mount and imaged on a Zeiss 510 NLO LSM confocal microscope. 2D cultured cells were stained identically with minor changes. After methanol fixation, cells were permeabilized with 0.2% (v/v) Triton X-100 for 10 min and washed twice with 1×PBS before blocking. Stained cells were covered with Gel Mount (Biomeda Corporation, Foster City, Calif.) and imaged by confocal microscopy. 2.5D hydrogels were stained in the same way as cultured cells. After staining, hydrogels were removed from culture inserts and placed cell-side down in 8-well chamber slides (Lab-tek® Products, Nalge Nunc International, Naperville, Ill.), covered with Gel Mount. 3D hydrogels were stained similarly. Each step during the staining of 3D hydrogels was prolonged by 50% to allow complete diffusion of liquids through the hydrogel. Cells on hydrogels were imaged by confocal microscopy. Negative controls omitted primary antibody. Primary antibodies specific for antigens expressed by other cell types present in the same tissues or cells served as negative controls for non-specific binding.

Functional Response: Exocytic Granule Production

Cells seeded ($1\times10^5$ cells/gel) on/in hydrogels were treated with varying concentrations (10 μM to 100 μM) of isoproterenol hydrochloride (Santa Cruz Biotechnology) and norepinephrine hydrochloride (Sigma), each of which induce granule production and exocytosis, for various time points from 15 min-2 h. After treatment, culture medium was removed and cells were fixed immediately with 100% methanol and stained with α-amylase for microscopic analysis.

Functional Response: Calcium Release Studies

Intracellular calcium [$Ca_i$] release studies utilized the calcium indicator dye, Fluo-4 (Invitrogen). Cells were seeded at $1\times10^5$ cells/gel in cell culture inserts as before. Cells on 2.5D and in 3D hydrogels were cultured for 12 days. Fluo-4 was suspended in 0.8% (w/v) pluronic acid and mixed with 8 mL of 1× Hanks' balanced salt solution (HBSS) without calcium. Cell-seeded hydrogels were incubated with Fluo-4 suspended in pluronic acid for 30 min at 37° C. After 30 min, cells were washed twice with 1×HBSS, and incubated for 30 min in HBSS. After loading and recovery, hydrogels were imaged using a Zeiss LSM 5-live high-speed confocal microscope. Baseline fluorescence was established for 30 sec at 488 nm. Cell-seeded hydrogels then were treated with various concentrations (ranging from 50 μM-500 μM) of the muscarinic agonist acetylcholine chloride. 2.5D hydrogels were flipped so that cells were on the bottom of the chamber slides. 50 μL of the agonist was added to the bottom of the chamber containing 50 μL medium. 3D hydrogels were suspended in 100 μL of medium and treated with 100 μL of agonist. Resulting increases in $Ca_i$ levels were captured in a series of image scans and by graph plot.

Animal Studies

Animal studies were performed as approved by the IACUC at the University of Delaware. Hydrogel biocompatibility studies used immunocompetent three-month old male Sprague Dawley rats to ensure that hydrogel material was not immunogenic and biodegraded over time. Male athymic hooded rats (Harlan Laboratories) aged 3-4 months were used for all implantation studies involving human cells. Rats were anesthetized in a closed chamber, purged with 0.5-1.0 L/min oxygen supplemented with 3-5% isoflurane, and kept asleep using a nose cone at 0.5-1.0 L/min oxygen with 1-3% isoflurane. Backs were shaved and cleaned with alcohol wipes, and subsequent surgical procedures conducted under a laminar flow hood. A 1 cm incision was made on the back and a small pocket was created for the implant. The 2.5D hydrogel was wrapped with a piece of electrospun gelatin membrane to avoid dispersion of cells cultured on it. Fabrication of electrospun gelatin scaffolds has previously been described (Sisson 2010 and Sisson 2009). 25% gelatin (w/w) (courtesy of Eastman Kodak Corporation, Rochester, N.Y.) was dissolved in a solvent containing acetic acid (ACS reagent, 99.7%, Sigma Aldrich, Milwaukee, Wis.), ethyl acetate (Fisher Scientific, Pittsburgh, Pa.), and distilled water at a ratio of 60:10:30. The gelatin solution was incubated overnight at 37° C. and stirred for an hour before electrospinning. Electrospun scaffolds were generated using an electrospinning unit, consisting of a syringe pump (KD Scientific, Holliston, Mass.), a high-voltage power supply (Spellman, Hauppauge, N.Y.), and a rotating mandrel collector. The syringe pump generates a constant flow from the needle at 0.5 mL/h flow-rate. Electrospun scaffolds were crosslinked with glutaraldehyde (GA) (Electron Microscopy Sciences, Hatfield, Pa.) in the vapor phase for 19 h at a concentration of 25% (w/w). Electrospun scaffolds with a fiber diameter of 600+/−110 nm were used.

The 3D hydrogel was not wrapped as the cells were fully encapsulated inside the hydrogel. Hydrogels were inserted in the incisional pocket and wounds closed with surgical clips. Animals recovered and resumed activity post-surgery. Rats were sacrificed at 11 day, 3-week and 4-week time points and the implants removed for analysis. Three implants per time-point were used in this pilot study.

Results

Acini-Like Spheroid Formation in 3D HA-Hydrogels

Cells seeded in 3D hydrogels self-assembled into organized acini-like spheroids within 3 days. Spheroids grew until a critical size of ~50 μm (~day 12) was reached, after which they merged and proliferated to form even larger structures (60-200 μm) (FIG. 18C, D). The progression of the growing acini-like structures is shown in FIGS. 18A-D. Tight junction proteins such as CL-1, ZO-1, E-cadherin, and adherens junction proteins such as β-catenin hold these spheroids together (FIG. 18A-D). Spheroids larger than 40 μm in diameter showed evidence of lumen formation via apoptosis of central cells (FIG. 18E). A representative brightfield image of an acinus-like structure is shown in FIG. 18F.

Growth of Acini-Like Structures in HA Hydrogels

Self-assembled acini-like structures formed within 1-3 days of culture in both the 2.5D and the 3D hydrogel systems and continued proliferating (FIG. 19). Acini-like structures grew more quickly in 3D than in 2.5D. At a critical density, the acini-like structures in the 3D culture system began to merge and the number of spheroids plateaued (FIG. 19). Cells seeded at a higher density in the hydrogels merged quicker and formed larger spheroids. However, these spheroids often were less organized than those seeded at lower densities. Spheroids in 3D were stable over 100 days and structures as large as 500 μm were observed. Structures in 2.5D rarely merged, were less organized, and grew much slower than those in 3D (FIG. 19).

Proliferation of acini-like structures in 3D was measured by quantifying their dsDNA over time as well as via staining with the proliferation marker, Ki67 (FIG. 19B, C, D). A linear increase in proliferation was observed among cells growing in 3D HA hydrogels (FIG. 19B). Acini-like structures cultured for over 48 days in 3D continued to proliferate (FIG. 19D). Ki67 staining was observed in cells located near the periphery of the structures (FIG. 19C, D).

Profiling Expression of Neurotransmitter Receptors in Glandular Tissue and Cultured Cells in 2D, 2.5D and 3D We profiled expression of the neurotransmitter binding receptors present on salivary acinar-like cells that activate pathways associated with salivary fluid secretion and protein synthesis. Salivary gland tissue sections, cells cultured in 2D, 2.5D, and those encapsulated in 3D were stained for neuroreceptors. Acinar-like cells cultured in 2D showed diffuse cytoplasmic expression of β1 and β2 adrenergic receptors, while the M3 muscarinic receptor was seen on the cell membranes of some acinar-like cells in 2D (FIG. 20A, B, C). Self-assembled salivary acinar-like cells cultured on 2.5D hydrogels expressed the β2 and M3 receptors in the cytoplasm and on the cell membranes (FIG. 20E, F). β1 receptor expression was seen on the cell membrane of some acinar-like cells in 2.5D (FIG. 20D). Organized spheroid structures encapsulated in 3D expressed all three receptors on their basolateral membranes (FIG. 20G, H, I). Some M3 muscarinic receptor was expressed on the lateral membranes of cells (FIG. 20I). As expected, glandular tissue sections showed expression of β1, β2 and M3 muscarinic receptors on the cell membranes (FIG. 20J, K, L). As seen among 3D spheroids, expression of M3 muscarinic receptor was seen along lateral membranes of glandular cells in tissue (FIG. 20L). The encapsulated acini-like structures in 3D were more organized and better able to localize the receptor for stimulation by neurotransmitters.

Stimulating Protein Secretion by Activating β Adrenergic Receptors

Functionality of salivary acinar-like cells was assessed by response to neurotransmitter agonists. Norepinephrine binding to the β adrenergic receptors activates the protein secretion pathway. In this study, the sympathomimetic β adrenergic agonists, norepinephrine and isoproterenol, were used to stimulate protein production and exocytosis. Salivary acinar-like cells cultured on/in hydrogels were treated with 50 μM isoproterenol for 15 min to 1 hr. After treatment, cells were immediately fixed and stained, then analyzed for granule formation and α-amylase expression. FIGS. 21-25 quantify the extent of amylase response, using the intensity of fluorescence staining as a surrogate. Untreated acinar-like cells in 2.5D and 3D showed a basal level of secretory granules and α-amylase staining (FIG. 21A, D). Cells treated with 50 μM isoproterenol for 15 min showed α-amylase near the membrane periphery, indicative of exocytosing vesicles (data not shown). Self-assembling structures with 1 h isoproterenol treatment showed the presence of granules and robust α-amylase staining in their secretory route in both 2.5D and 3D (FIG. 21B, E). Self-assembling acini-like structures treated with 50 μM norepinephrine also displayed multiple secretory granules in both 2.5D and 3D (FIG. 21C, F). Exocytosing granules stained in red for α-amylase are seen budding out from the cell membrane in FIG. 21C, E, F. Granule production has been quantified in FIG. 26. Upon stimulation, acini-like structures in 3D also secreted α-amylase into the hydrogel (FIG. 21E, F). α-Amylase staining is quantified in FIGS. 23-25. This indicates that cells in 3D produce detectable levels of salivary proteins that can be secreted upon stimulation unlike those in 2.5D. Neurotransmitter treatment was repeated >3 times and representative images are shown in FIG. 21. Over 50% of the cells in the treated samples displayed granules.

Stimulating Fluid Secretion by Activation of M3 Muscarinic Receptors

To stimulate fluid secretion, salivary acinar-like cells were treated with acetylcholine. Addition of 50 μM acetylcholine induced a robust calcium response in self-assembling acini-like structures cultured on 2.5D hydrogels (FIG. 27A). Acini-like structures on hydrogels were imaged without saline buffer to minimize movement of hydrogels in the liquid. The calcium response peak seen at ~5 min can be attributed to the diffusion time needed by the neurotransmitter to pass through the hydrogel to the cells. Treatment with 100 μM acetylcholine produced calcium oscillations lasting over 20 min in multiple cells within a self-assembled acinus-like structure (FIG. 27B). Oscillations from different structures varied in intensity. Single cells that were not assembled into structures did not respond to the agonist. Experiments were performed three times with each agonist concentration, on separate hydrogel cultures. Data were recorded from 3-4 acini-like structures each time. Representative data sets are shown in FIGS. 27A and 27B. A representative confocal image of stimulated cells in 2.5D is shown in FIG. 27C. Negative controls performed with addition of saline buffer in place of the agonist failed to induce a calcium response. Positive controls used a hypotonic solution to induce a calcium response.

Treatment with 50 μM acetylcholine induced calcium oscillations that lasted over 20 minutes in spheroid structures encapsulated in 3D hydrogels (FIG. 27D). Acetylcholine (100 μM) induced similar oscillations among the 3D cultures (FIG. 27E). Compared to the response seen among 2.5D cultures, the increase in $[Ca^{2+}]$ was quicker in 3D, where cells responded to acetylcholine treatment within 30 seconds while cells in 2.5D took nearly 300 seconds. The duration of the oscillations was significantly longer in the 3D cultures than in 2.5D suggesting that the apical calcium channels might be open longer, allowing for enhanced fluid secretion (Table 1). A representative confocal image of responding cells in 3D is shown in FIG. 27F. Thus, cell response to acetylcholine agonist in 3D was faster, more intense, and more prolonged than cell response in 2.5D.

Structures are Preserved in Hydrogels when Implanted In Vivo.

TABLE 1

Intracellular calcium release data from acini-like structures treated with acetylcholine (ACh).

| Sample | Percent Responders | Average Peak Height (Intensity) | Average Peak Length(s) |
| --- | --- | --- | --- |
| 2.5D 50 μM ACh | 33% | 58 ± 11 | 42 ± 21 |
| 2.5D 100 μM ACh | 22% | 10 ± 3 | 46 ± 9 |
| 3D 50 μM ACh | 43% | 39 ± 6 | 164 ± 8 |
| 3D 100 μM ACh | 16% | 14 ± 8 | 180 ± 34 |

To evaluate the long-term survival of the acini-like structures on 2.5D and those encapsulated in 3D hydrogels in vivo, cell-seeded 2.5 and 3D scaffolds were implanted in an athymic rat model. To avoid dispersion of cells from the 2.5D hydrogel scaffold, the hydrogel with cells was wrapped in an electrospun gelatin membrane. 3D cell-seeded scaffolds were implanted without wrapping. Implants were analyzed at 11 days and 3 weeks. Some blood vessel infiltration (arrows) was seen within both implants in 2.5D and 3D (FIG. 28A-B, D-E). Despite the presence of the gelatin membrane, the cells in the 2.5D hydrogel scaffold lost their assembly in acini-like structures and dispersed as single cells in the rat tissue surrounding the implant (FIG. 28C). Encapsulated acini-like structures in the 3D scaffold remained intact in their spheroid structures within the hydrogel for over 3 weeks (FIG. 28F), survived implantation in vivo, and continued to produce α-amylase.

Discussion

A biodegradable and human-compatible scaffoldable to support growth and differentiation of human salivary gland cells into functional salivary units that secrete fluid and protein upon stimulation is a key step toward creation of an artificial salivary gland. Previously we reported the isolation of human salivary acinar cells that self-assemble into acini-like structures and express salivary biomarkers when cultured on ECM derived human-compatible biomimetic peptides. To better mimic the in vivo environment, we developed an HA-based, 2.5D hydrogel culture system that can support the growth and partial differentiation of 3D acini-like structures in vitro, but cannot be used to encapsulate cells.[6] We now report conversion of our 2.5D model to a fully 3D culture system that promotes organized growth and differentiation of salivary acinar-like cells into functional acini-like structures and fosters their long-term survival in the 3D scaffold in vivo as well as in vitro. It should be noted that the 3D gels we used to encapsulate the cells are softer (G'~68 Pa) than the 2.5D gels (G'~1490 Pa) and they contain polyethylene glycol, but they allow full encapsulation of primary cells.

Groups that reported salivary acini-like structures or spheroids growing in 2D or 2.5D obtained less well organized salivary structures compared to those seen in 3D cultures. Our results are consistent with this observation, and suggest that dimensionality determines the organized assembly of complex structures as much or more than gel composition. Additionally, most of these 3D salivary cultures used Matrigel™, collagen I or other animal derived products for their scaffolds. The human-compatible 3D culture system reported here supports the growth of organized spherical structures that merge to form larger acini-like structures with a central lumen and can be maintained long-term in vitro. These stable spheroid structures expressed essential salivary biomarkers and neurotransmitter receptors. The presence of β adrenergic and M3 muscarinic receptors on acinar-like cells in 3D suggested that these cells can activate fluid and protein transport upon treatment with neurotransmitters.

Saliva contains an array of protein components that provide saliva with its anti-bacterial, anti-viral, anti-fungal, lubricative, digestive and buffering qualities. α-Amylase, one of the most abundant proteins in saliva, is an essential enzyme that breaks down starch and initiates digestion. Acini-like structures in both 2.5D and 3D hydrogels increased production of α-amylase positive granules upon stimulation with norepinephrine and isoproterenol, indicating a functional protein secretion pathway was present. While a robust increase in the secretion of amylase and its accumulation in the hydrogel were promising, it also indicated a reverse polarity among many of the structures. Staining with MUC1 (a marker of polarity) revealed that only a few structures had luminal MUC1 (not shown). Lessons from studies with mammary gland acini suggest that cues from the ECM and the encasing myoepithelial cells are needed to reverse inside-out acini and attain correct polarity, a final step in functional assembly of the salivary gland. Co-cultures with salivary myoepithelial cells may correct the acini polarity and ensure unidirectional secretion into the ductal lumen.

Fluid secretion is an important function of salivary acini where it aids essential oral functions including mastication and speech. Several reports showed increases in $Ca_i$ upon treatment with acetylcholine (or carbachol) in parotid or submandibular acini and dissociated cells. Here we demonstrated the induction of calcium oscillations upon neurotransmitter stimulation of 3D acini-like spheroids in a human-compatible hydrogel culture system. The increase in $Ca_i$ and the recurring oscillations induced by acetylcholine among our 2.5D and 3D cultures indicates a functional fluid production pathway. Calcium oscillations have been reported by carbachol treatment of intact parotid acini, indicating that our 3D spheroids resemble glandular acini, functionally. Variability in intensity of the calcium response among cells in 2.5D reflects the lack of uniform organization among the structures in 2.5D. Spheroids in 3D were more organized and responded to stimulation better than the less-organized structures in 2.5D. Gap junctions among salivary acinar cells can induce synchronous calcium responses by cells within an acinus. It is likely that the organized acini-like structures in 3D respond better and more consistently because they possess gap junctions indicating cellular connectivity.

Branching morphogenesis is a key step in the development of the salivary gland. Parasympathetic innervation occurs early in the developing salivary gland and an interaction of the nerves with the salivary gland parenchyma is critical for further gland development. It was reported recently that removal of the parasympathetic ganglion during early salivary gland development reduces progenitor cell populations, which could be rescued with carbachol, an acetylcholine analog (Knox et al., 2010). Thus, treatment with muscarinic agonists can aid in branching morphogenesis and further development of salivary glands.

A major challenge in the field of tissue engineering is necrosis of implants in vivo. To ensure survival of our implant in vivo, we performed a series of animal studies with our 2.5D and 3D hydrogels. Implantation studies showed long-term survival and maintenance of spheroid structures in 3D but dispersal of cells in 2.5D. We believe these cells in 3D can be maintained for a longer time in the presence of the protective hydrogel and more normal cell-cell interactions.

Although the 3D system reported here reflects an important advance because it produces protein and fluid upon stimulation, it still lacks essential machinery for full salivary restoration. Future studies can incorporate ductal and myoepithelial cells to form complete functional polarized salivary units with assembled ductal structures that can modify and transport salivary fluid. The studies reported here provide strong evidence that we can develop a functional, neurotransmitter responsive artificial gland that can be incorporated into the buccal mucosa or native salivary gland of patients to restore both fluid and salivary proteins present in saliva.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A hydrogel network comprising: a hyaluronic acid macromer crosslinked with a crosslinker, wherein the crosslinker is a multiblock copolymer, wherein the multiblock copolymer comprises an alternating copolymer of poly(ethylene glycol) (PEG) and a peptide epitope of perlecan, or an alternating copolymer of poly(acrylic acid) and a hydrophobic peptide.

2. The hydrogel network of claim 1, wherein the multiblock copolymer comprises a multiblock copolymer of perlecan domain IV (P1nDIV) peptide alternating with PEG.

3. The hydrogel network of claim 1, wherein the multiblock copolymer comprises a multiblock copolymer of poly(acrylic acid) alternating with a hydrophobic peptide of sequence $(VPGVG)_2$.

4. The hydrogel network of claim 1 wherein the hydrogel network is biocompatible.

5. A kit comprising a hyaluronic acid macromer and a crosslinker, wherein the crosslinker is a multiblock copolymer, wherein the multiblock copolymer comprises an alternating copolymer of poly(ethylene glycol) and a peptide epitope of perlecan, or an alternating copolymer of poly(acrylic acid) and a hydrophobic peptide.

6. The kit of claim 5 wherein the hyaluronic acid macromer comprises an unsaturated double bond.

7. The kit of claim 5 wherein the hyaluronic acid macromer comprises an acrylate.

8. The kit of claim 5 further comprising hyaluronic acid hydrogel particles.

9. The kit of claim 8 wherein the hyaluronic acid hydrogel particles further comprise a growth factor.

10. The kit of claim 8 wherein the hyaluronic acid hydrogel particles are angiogenic.

11. A method of forming a hydrogel network comprising: providing a hyaluronic acid macromer; providing a crosslinker, wherein the crosslinker is a multiblock copolymer comprising an alternating copolymer of PEG and a peptide epitope of perlecan, or an alternating copolymer of poly(acrylic acid) and a hydrophobic peptide, and crosslinking the hyaluronic acid macromer with the crosslinker to form the hydrogel network.

12. The method of claim 11, wherein the multiblock copolymer comprises a multiblock copolymer of P1nDIV peptide alternating with PEG.

13. The method of claim 11, wherein the multiblock copolymer comprises a multiblock copolymer of poly(acrylic acid) alternating with a hydrophobic peptide of sequence (VPGVG)2.

14. The method of claim 11 further comprising encapsulating cells within the hydrogel network.

15. The method of claim 11 further comprising encapsulating hyaluronic acid hydrogel particles within the hydrogel network.

16. The method of claim 11 wherein two or more hydrogel networks are combined to form a secondary hydrogel network.

17. The method of claim 16 wherein the secondary hydrogel network is a 3D construct.

18. A method of constructing a biomimetic matrix comprising:
providing a hyaluronic acid hydrogel network comprising a hyaluronic acid macromer crosslinked with a crosslinker, wherein the crosslinker is a multiblock copolymer comprising an alternating copolymer of poly(ethylene glycol) (PEG) and a peptide epitope of perlecan, or an alternating copolymer of poly(acrylic acid) and a hydrophobic peptide;
providing hyaluronic acid hydrogel particles;
providing salivary cells; and
co-encapsulating the hyaluronic acid hydrogel particles and the salivary cells within the hyaluronic acid hydrogel network to form cell-laden microgel modules.

19. The method of claim 18, further comprising: combining multiple cell-laden microgel modules into a secondary hyaluronic acid network to yield a 3D network.

20. The method of claim 18 wherein the cells are treated with at least one of a $\beta$-adrenergic agonist, a M3 muscarinic agonist, and combinations thereof.

21. A composition comprising: a hyaluronic acid macromer; a crosslinker comprising a multiblock copolymer comprising a copolymer of P1nDIV peptide alternating with PEG; and hyaluronic acid hydrogel particles.

22. The composition of claim 21 further comprising cells.

* * * * *